United States Patent
Smidt et al.

(10) Patent No.: US 9,527,796 B2
(45) Date of Patent: Dec. 27, 2016

(54) PROCESS FOR THE PREPARATION OF SUCCINIC ACID ESTER

(71) Applicant: Johnson Matthey Davy Technologies Limited, London (GB)

(72) Inventors: Martin Lucas Smidt, London (GB); Ian Campbell, London (GB); Graham Reed, London (GB); Paul Gordon, Durham (GB); Christopher Ferguson, Durham (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

(21) Appl. No.: 14/785,113

(22) PCT Filed: Dec. 2, 2014

(86) PCT No.: PCT/GB2014/053588
§ 371 (c)(1),
(2) Date: Oct. 16, 2015

(87) PCT Pub. No.: WO2015/082915
PCT Pub. Date: Jun. 11, 2015

(65) Prior Publication Data
US 2016/0264508 A1 Sep. 15, 2016

(30) Foreign Application Priority Data
Dec. 6, 2013 (GB) .................................. 1321627.0

(51) Int. Cl.
C07C 67/08 (2006.01)
C07C 67/54 (2006.01)
B01D 3/00 (2006.01)
B01D 3/14 (2006.01)
B01D 17/02 (2006.01)

(52) U.S. Cl.
CPC .............. C07C 67/08 (2013.01); B01D 3/009 (2013.01); B01D 3/143 (2013.01); B01D 17/0208 (2013.01); C07C 67/54 (2013.01)

(58) Field of Classification Search
CPC ..... C07C 67/08; C07C 67/54; B01D 17/0208; B01D 3/009; B01D 3/143
See application file for complete search history.

(56) References Cited

U.S. PATENT DOCUMENTS

| | | |
|---|---|---|
| 3,830,830 A | 8/1974 | Cleveland et al. |
| 4,584,419 A | 4/1986 | Sharif et al. |
| 4,656,297 A | 4/1987 | Kouba et al. |
| 4,751,334 A | 6/1988 | Turner et al. |
| 4,767,869 A | 8/1988 | Harrison et al. |
| 4,794,824 A | 1/1989 | Chapman |
| 4,795,824 A | 1/1989 | Kippax et al. |
| 4,919,765 A | 4/1990 | Wilkes et al. |
| 4,945,173 A | 7/1990 | Wood |
| 5,254,758 A | 10/1993 | Hiles et al. |
| 5,310,954 A | 5/1994 | Hiles et al. |
| 5,723,639 A | 3/1998 | Datta et al. |
| 5,958,744 A | 9/1999 | Berglund et al. |
| 6,265,790 B1 | 7/2001 | Vogman |
| 7,816,554 B2 * | 10/2010 | Sutton .................. C07C 29/177 560/204 |
| 8,246,792 B2 | 8/2012 | Fruchey et al. |
| 8,410,306 B2 * | 4/2013 | Bauduin ............... C07C 29/149 560/180 |
| 8,889,898 B2 * | 11/2014 | Sainani .................. C07C 67/08 502/150 |
| 2013/0303796 A1 | 11/2013 | Hwang et al. |

FOREIGN PATENT DOCUMENTS

| | | |
|---|---|---|
| CN | 101323566 | 12/2008 |
| CN | 103342638 | 10/2013 |
| EP | 1849764 | 10/2007 |
| JP | 01-1216958 | 8/1989 |
| JP | 04-091055 | 3/1992 |

(Continued)

OTHER PUBLICATIONS

"Reaction Kinetics for the Heterogeneously Catalyzed Esterification of Succinic Acid with Ethanol" Kolah A K et al Ind. Eng. Chem. Res., 2008, 47(15) pp. 5313-5317.
"Pervaporation-assisted Esterification of Lactic and Succinic Acids with Downstream Ester Recovery" Benedict et al, J. Membrane Sci., 2006, 281 pp. 435-445.
"Combined Technology of Catalytic Esterification and Absorption of Succinic Acid" Ding B et al the Chinese Journal of Process Engineering, pp. 100-104, 2007-02-20 (Abstract Only).
"Preparation of Diethyl Succinate by Catalytic Esterification and Absorption Dehydration" Gong C et al China Surfactant Detergent & Cosmetics, pp. 245-248, 2008-04 (Abstract Only).
"Purification of succinic acid from synthetic solution using vapor permeation-assisted esterification coupled with reactive distillation", A Boontawan, Advanced Materials Research, vols. 550-553, pp. 3008-3011, Jul. 2012.

(Continued)

Primary Examiner — Shailendra Kumar
(74) Attorney, Agent, or Firm — Armstrong Teasdale LLP

(57) ABSTRACT

A process for the production of dialkyl succinate from a bio-succinic acid feedstock commencing by feeding bio-succinic acid to a reaction distillation column to enable esterification of the succinic acid. The feedstock is passed co-currently with upflowing alkanol such that an esterification reaction occurs. An overhead vapor stream is removed from the reaction distillation column comprising di-ester, alkanol, water of esterification and organic components. The vapor stream is sent to an alkanol separation column where alkanol is separated from the water of esterification and organic components. A side draw is removed from the alkanol separation column comprising partially immiscible organic and aqueous phases. The side draw is passed to a phase separation apparatus where the partially immiscible organic and aqueous phases are separated. The organic phase is passed to a column where the dialkyl succinate is recovered from residual water and other organic components.

29 Claims, 16 Drawing Sheets

(56) References Cited

FOREIGN PATENT DOCUMENTS

| WO | 86/03189 | 6/1986 |
|---|---|---|
| WO | 88/00937 | 2/1988 |
| WO | 90/08127 | 7/1990 |
| WO | 91/01960 | 2/1991 |
| WO | 99/35113 | 7/1999 |
| WO | 99/35136 | 7/1999 |

OTHER PUBLICATIONS

"Diethyl succinate synthesis by reactive distillation", pp. 151-162, ISSN: 1383-5866, Separation and Purification Technology, vol. 88, 2012, (Orjuela, Alvaro et al).

"A novel process for recovery of fermentation-derived succinic acid", pp. 31-37, ISSN: 1383-5866, Separation and Purification Technology, vol. 83, 2012, (Orjuela, Alvaro et al).

"Mixed Succinic Acid/Acetic Acid Esterification with Ethanol by Reactive Distillation", pp. 9209-9220, ISSN: 0888-5885, Industrial & Engineering Chemistry Research, vol. 50 (15), 2011, (Orjuela, Alvaro et al).

Towards a Bio-based Industry: Benign Catalytic Esterifications of Succinic Acid in the Presence of Water, Budarin et al vol. 13, Issue 24, pp. 6914-6919, Aug. 17, 2007.

Feasibility of Production Methods for Succinic Acid Derivatives; a Marriage of Renewable Resources and Chemical Technology; A Cukalovic et al Biofuels, Bioproducts and Biorefining vol. 2, issue 6, pp. 505-529, Nov./Dec. 2008.

Chemical Transformations of Succinic Acid Recovered from Fermentation Broths by a Novel Direct Vacuum Distillation—Crystallisation Method, R Lugue et al, Green Clem., 2009, 11, 193-200.

* cited by examiner

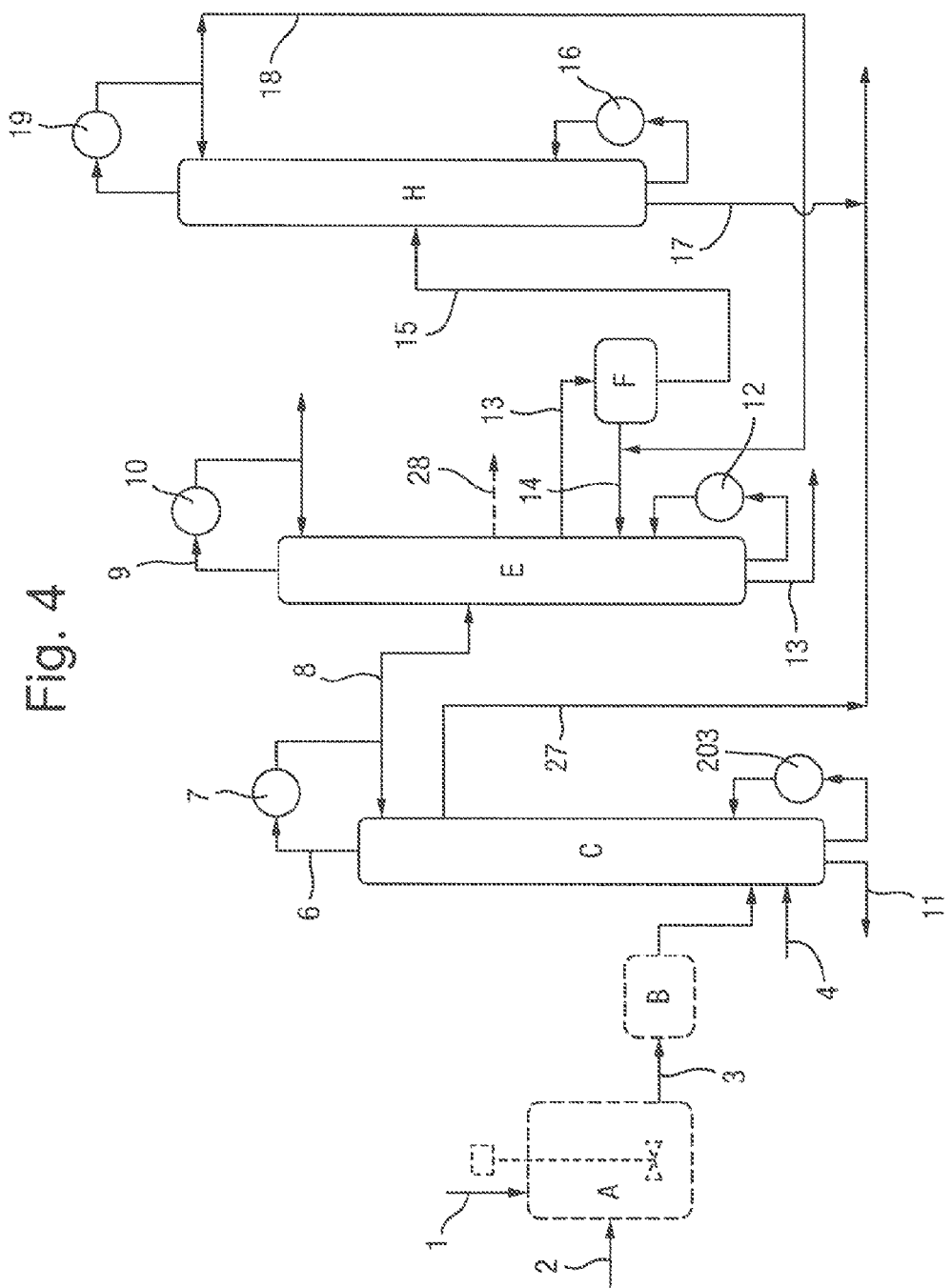

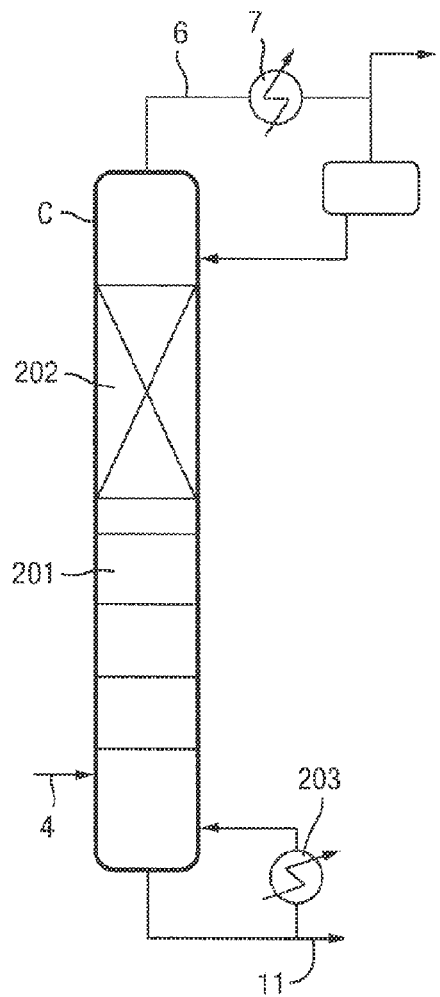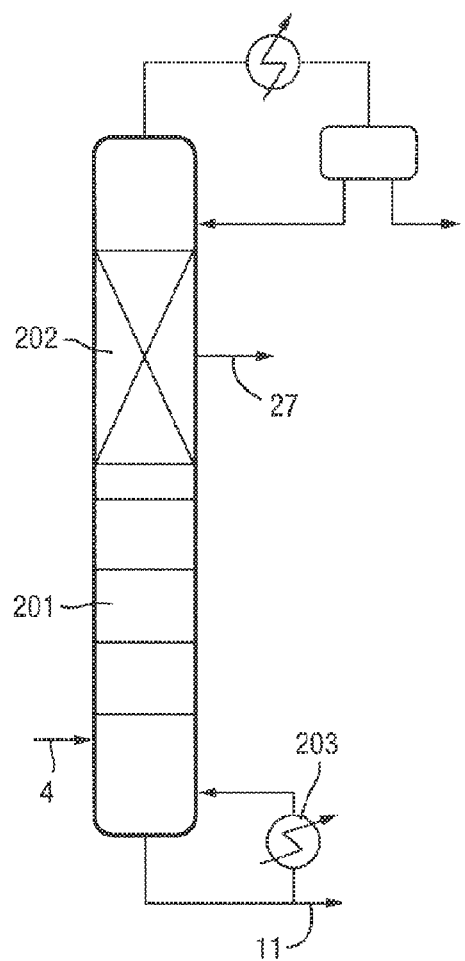

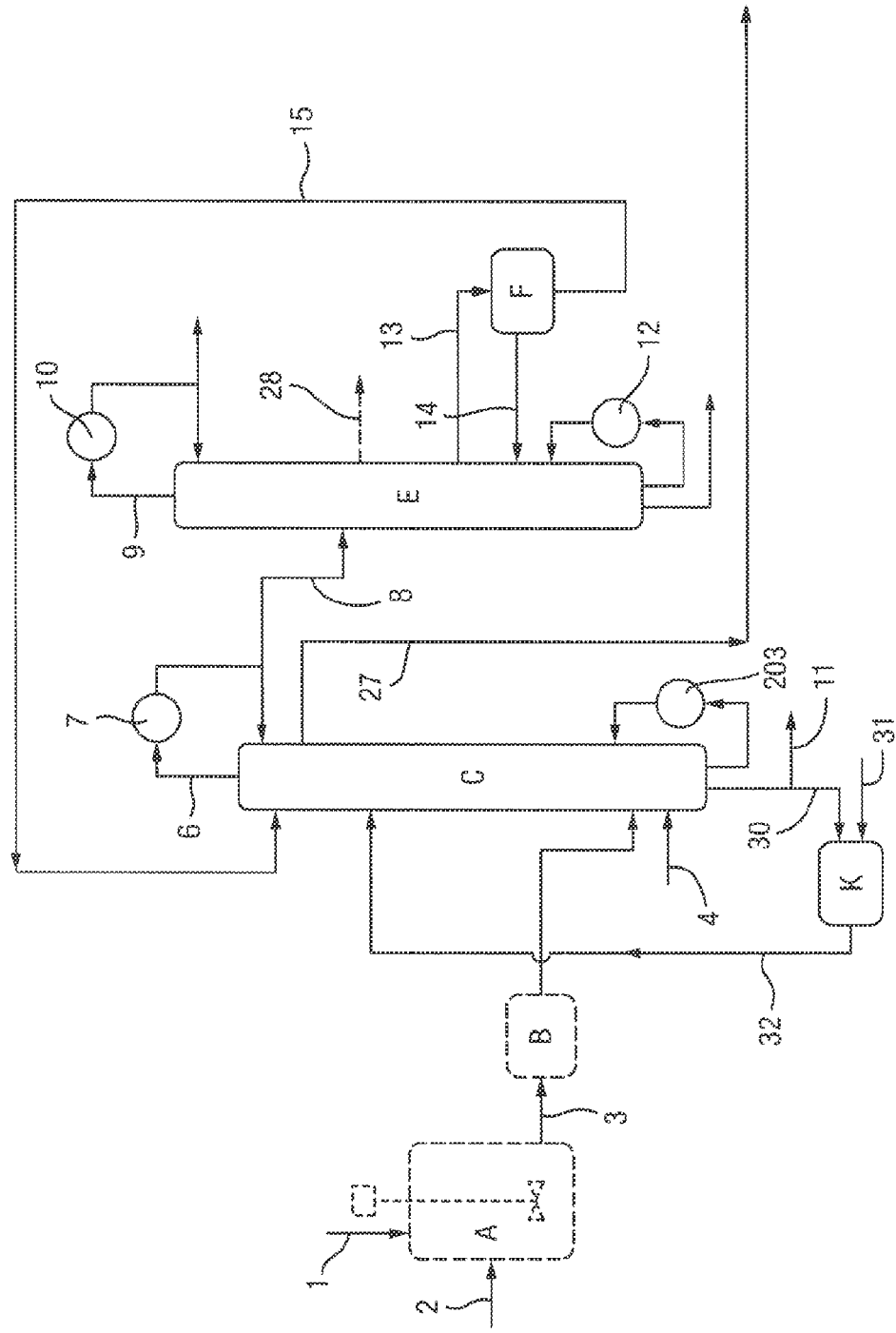

Catalyst Deactivation Testwork

Crude Bio-SAC MMS

Pure Bio-SAC MMS

Overheads Analysis

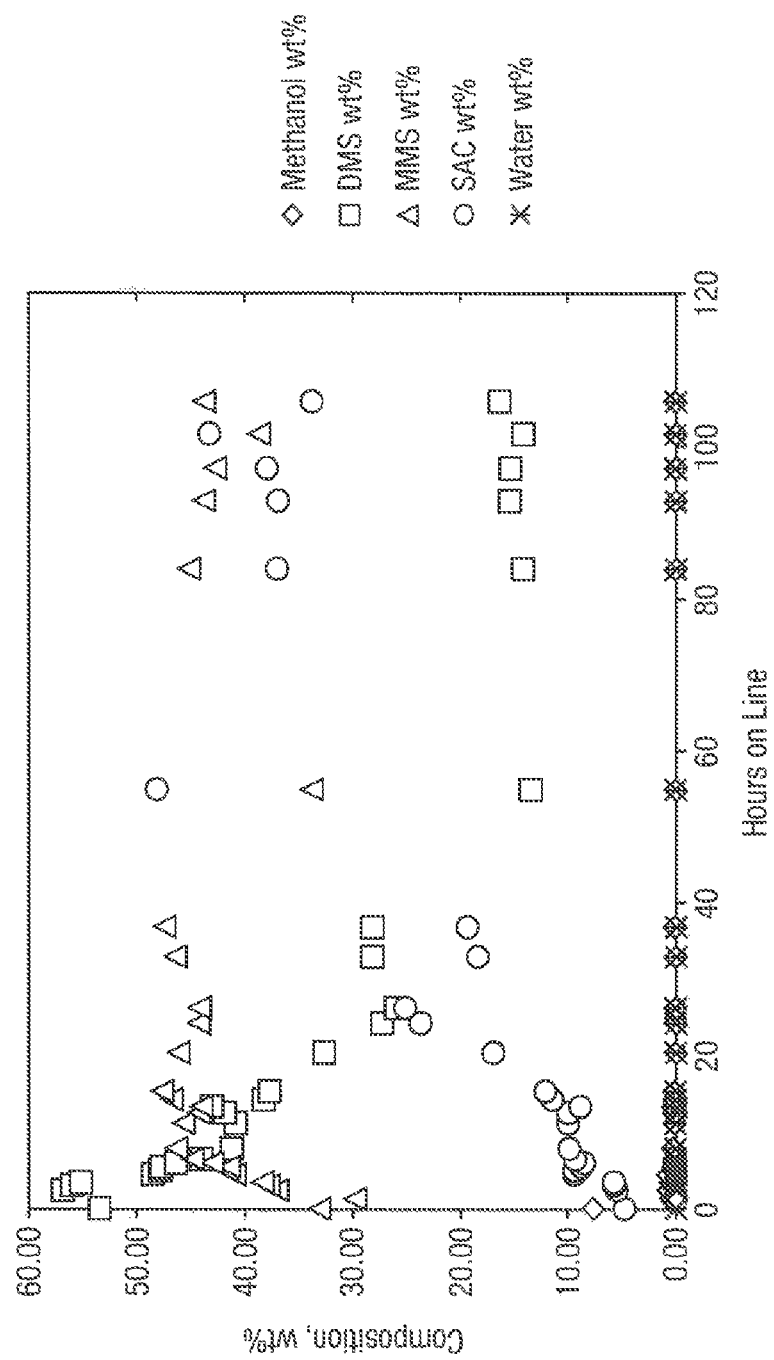

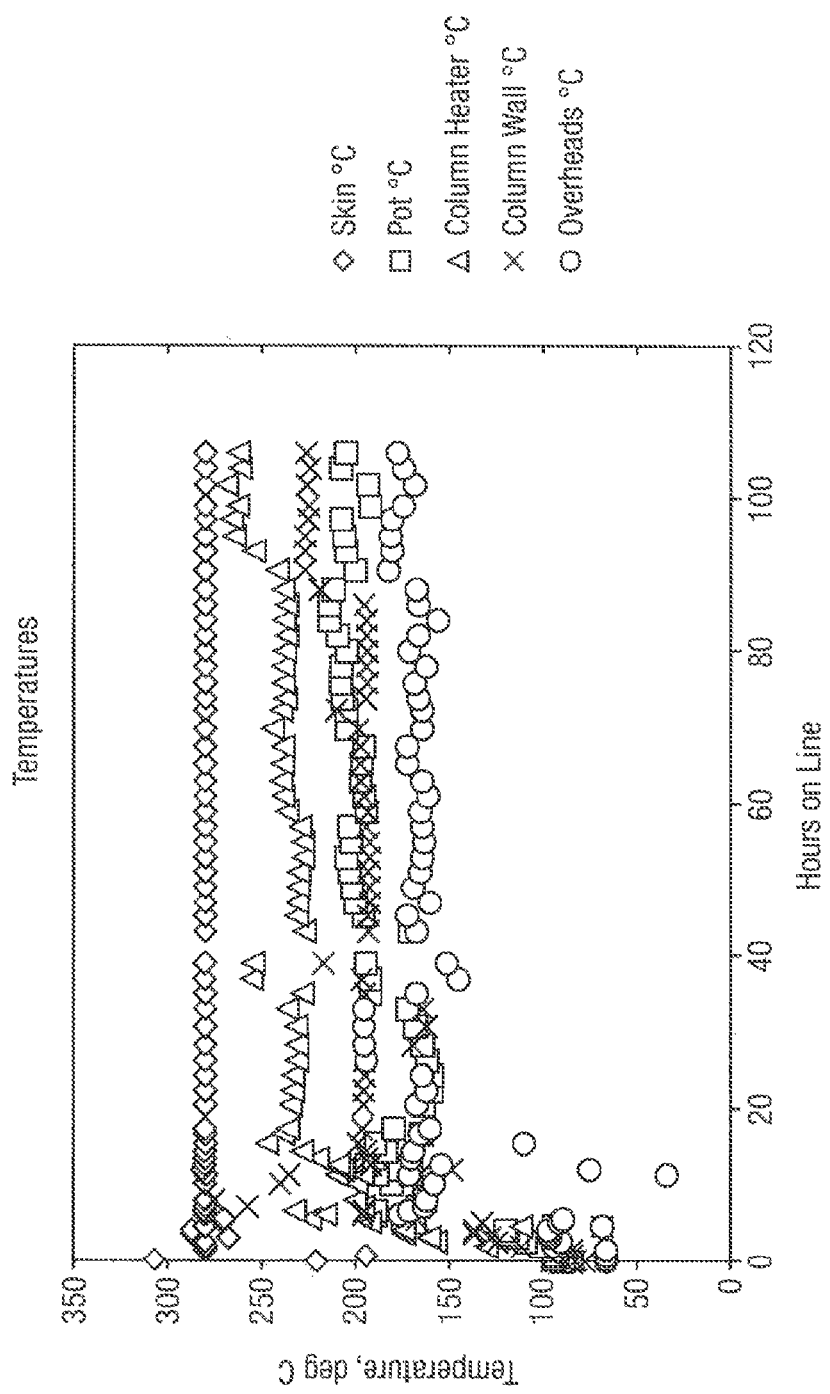

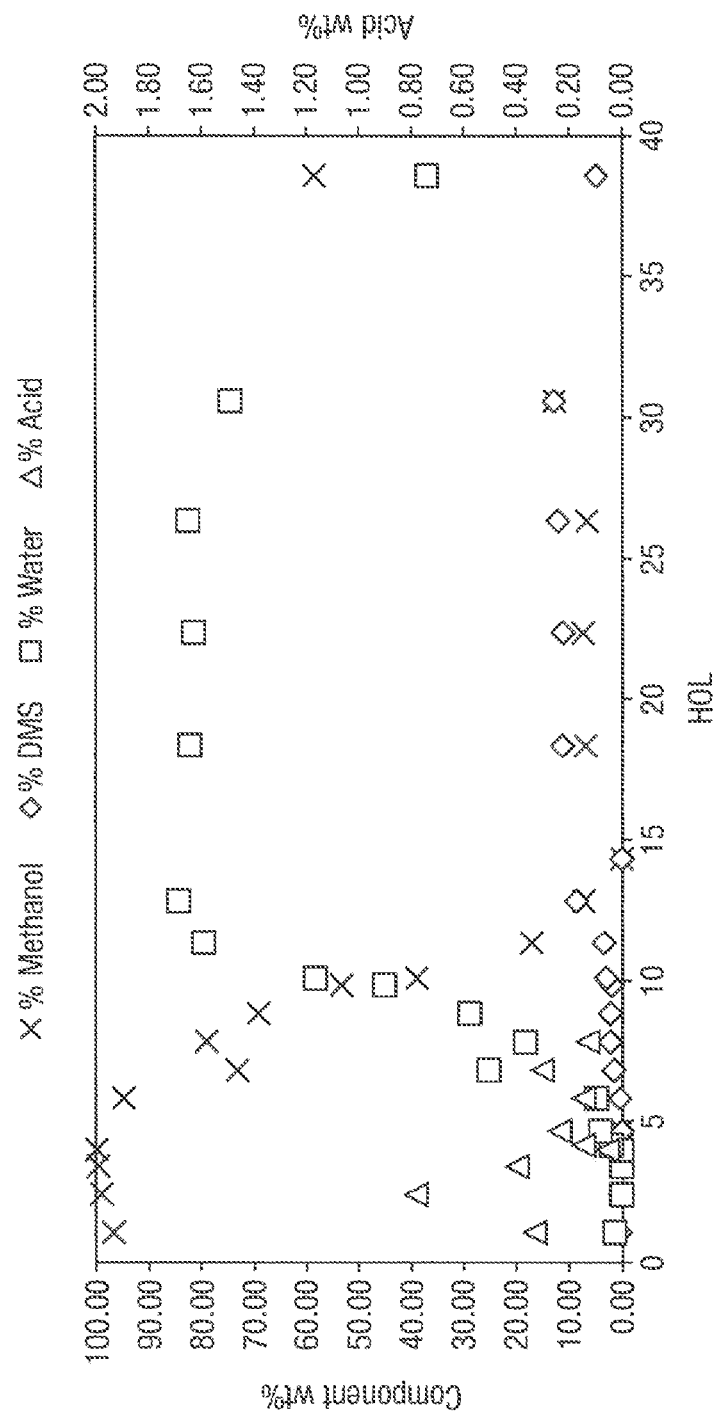

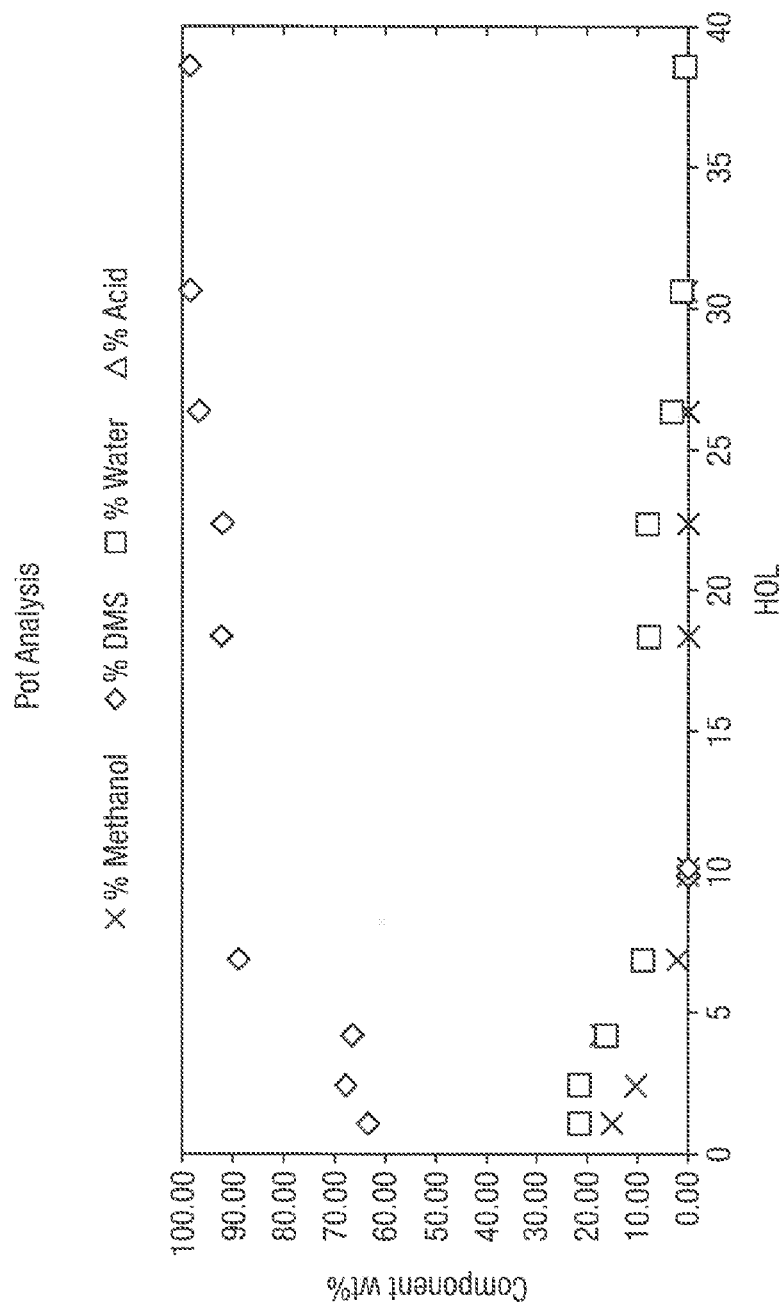

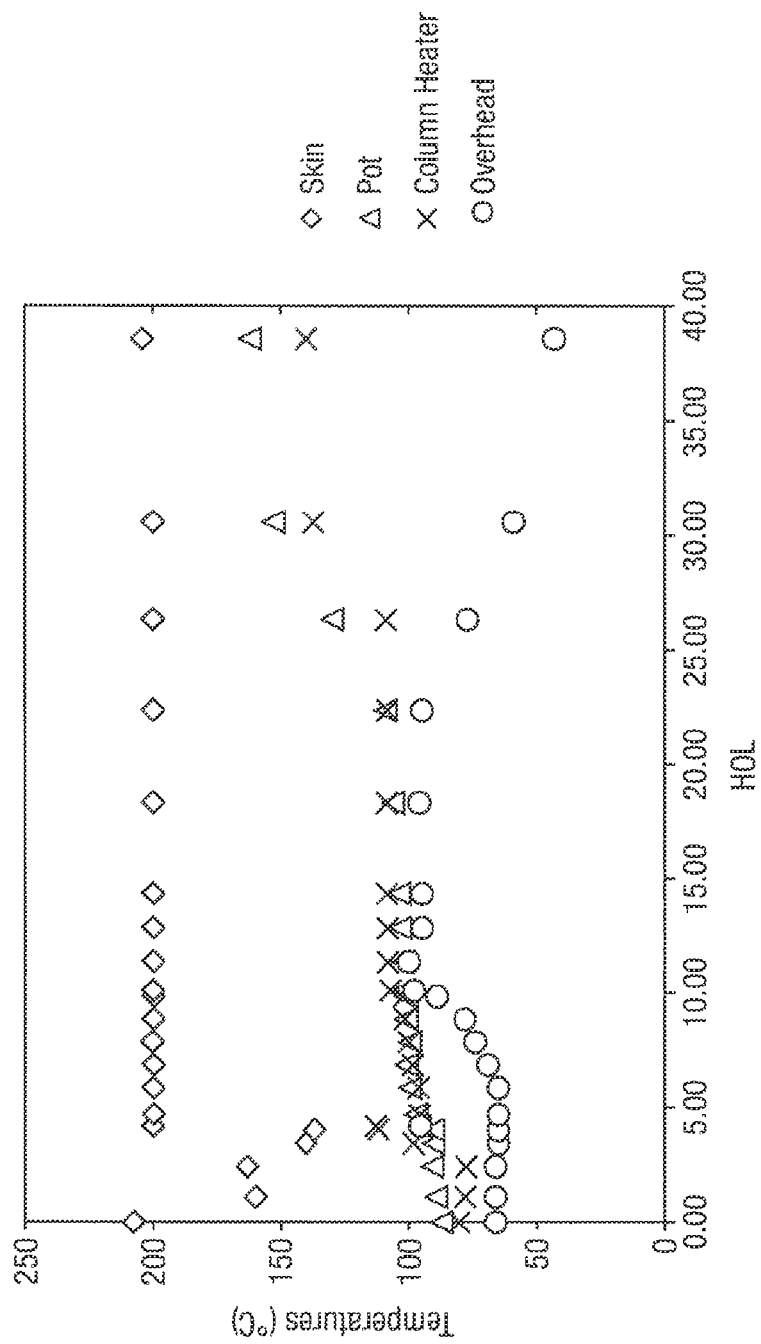

PROCESS FOR THE PREPARATION OF SUCCINIC ACID ESTER

This application is a 371 of PCT/GB2014/053588, filed on Dec. 2, 2014.

The present invention relates to a process for the production of dialkyl succinate from a feedstock comprising succinic acid produced by a fermentation based process.

It is known to produce diols by reaction of dicarboxylic acids and/or anhydrides, or mono- or di-alkyl esters, lactones, and mixtures thereof with hydrogen. Commercially, where the desired product is 1,4-butanediol, typically with the co-products tetrahydrofuran and γ-butyrolactone, the starting material is normally a dialkyl ester of maleic acid and/or anhydride, such as dimethyl maleate or diethyl maleate, which may contain minor amounts of dialkyl fumarate and/or dialkyl succinate.

Information relating to these processes can be found in, for example, U.S. Pat. No. 4,584,419, U.S. Pat. No. 4,751,334, WO86/03189, WO88/00937, U.S. Pat. No. 4,767,869, U.S. Pat. No. 4,945,173, U.S. Pat. No. 4,919,765, U.S. Pat. No. 5,254,758, U.S. Pat. No. 5,310,954 and WO91/01960.

The dialkyl maleates which are used as feedstock in these conventional reaction processes may be produced by any suitable means. The production of dialkyl maleates for use in such processes is discussed in detail in U.S. Pat. No. 4,584,419, U.S. Pat. No. 4,751,334, WO88/00937, U.S. Pat. No. 4,795,824 and WO90/08127.

In one conventional process for the production of 1,4-butanediol and co-product tetrahydrofuran with optional production of γ-butyrolactone, a dialkyl ester, such as dimethyl maleate together with any residual methanol from the esterification reactor, is fed to a vaporiser where it is vaporised by a stream of hot cycle gas fed to the vaporiser which may be mixed with make-up hydrogen. The cycle gas will normally contain a high concentration of hydrogen gas but may also include other gases including hydrocarbons, carbon oxides, methane and nitrogen. Further, where the cycle gas includes recycled gases from downstream, condensables including product ether, methanol, water, co-products and by-products may also be present.

The combined vaporous stream from the vaporiser is then passed to a reactor where it is reacted in the presence of a catalyst to form 1,4-butanediol, tetrahydrofuran and/or γ-butyrolactone. The product stream is cooled and the reaction products are condensed and separated from the excess cycle gas before being passed into a refining zone. In the refining zone the various products are separated and the 1,4-butanediol and the tetrahydrofuran are removed. The γ-butyrolactone, together with the intermediate, dimethyl succinate, and some 1,4-butanediol may be recycled. In one arrangement the γ-butyrolactone may be at least partially extracted in an optional refining zone and recovered. The methanol water stream separated from the product mix will be recycled upstream. In general, a significant portion of the 1,4-butanediol produced by this or other conventional methods is subsequently converted to tetrahydrofuran.

The overall reaction which occurs is a series of steps and includes a final dehydration step in which the tetrahydrofuran is produced. A probable reaction path is set out in Scheme 1.

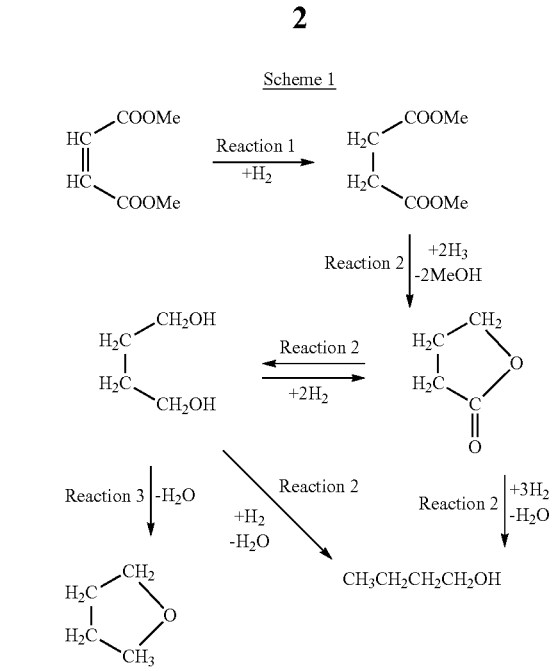

Scheme 1

An alternative process is described in WO99/35113 in which maleic anhydride esters are fed to a reaction process in which three different catalysts are used. First the maleate is converted to the succinate in the presence of the first catalyst which is a heterogeneous selective hydrogenation catalyst at a temperature of from 120° C. to 170° C. and a pressure of 3 to 40 bara. The succinate is then passed directly to the presence of the second catalyst where it is converted mainly into γ-butyrolactone. The product of the reaction with the second catalyst is then fed directly to the presence of a third catalyst which is used to dehydrate the γ-butyrolactone to produce tetrahydrofuran. Some of the γ-butyrolactone formed in the presence of the second catalyst is transferred to a second reaction loop operating at a higher pressure where it is converted to 1,4-butanediol.

As the first step in Scheme 1 and the first catalyst used in the alternative process described in WO99/35113 relates to the hydrogenation of the dimethyl maleate to dimethyl succinate, it has been suggested that dimethyl succinate or diethyl succinate may be suitable starting materials for the reaction with hydrogen to form 1,4-butanediol, tetrahydrofuran and/or γ-butyrolactone.

One process in which dimethyl succinate is used in the production of tetrahydrofuran and 1-4-butanediol is described in U.S. Pat. No. 4,656,297. In this process, methanol is added to the ester feed to increase conversion and reduce transesterification. Another example of a process in which dimethyl succinate is suggested as a feed is WO99/35136 in which reaction with hydrogen occurs over two different catalysts, to form a mixture of tetrahydrofuran and γ-butyrolactone.

Maleic anhydride is commonly produced commercially from benzene or n-butane, both of which are ultimately derived from crude oil. It is therefore desirable to look for alternative starting materials which are not derived from oil in an attempt to improve the environmental impact and potentially improve the economics.

Recently, there have been significant advancements in processes to produce and recover succinic acid from the fermentation of sugars. Examples of processes can be found in, for example, U.S. Pat. No. 5,958,744, U.S. Pat. No.

6,265,190 and U.S. Pat. No. 8,246,792. Currently demonstration plants have been constructed. It is anticipated that in due course such processes may be able to compete with maleic anhydride as an economic feedstock for the production of 1,4-butanediol.

Where succinic acid is used as the feedstock, it will generally first be esterified to produce dialkyl succinate. While the processes and plant described in U.S. Pat. No. 4,795,824 and WO90/08127 may be used to produce dialkyl succinates from succinic acid, there are various disadvantages and drawbacks.

The processes described in these prior art systems are not ideally suited to being carried out where the starting material is succinic acid. This is particularly the case where the succinic acid is produced by a fermentation process. For ease of reference, we will refer to succinic acid produced by fermentation processes as "bio-succinic acid" and the term should be construed accordingly.

Bio-succinic acid generally contains impurities. These may be fermentation residues and by-products. These impurities, which may include sulphur, may be detrimental to the operation of catalysts used in reactions which utilise this bio-succinic acid. This is particularly problematic where the subsequent reactions utilise a copper based catalyst. Another arrangement where the impurities are particularly detrimental is where the subsequent reaction uses an acid resin catalyst such as an esterification. Whilst it may be possible to address the problem by removal of these impurities by purification processes prior to contact with catalyst in the subsequent reactions, the number of steps required to produce succinic acid of sufficient purity are substantial. The requirement for these purification steps significantly increase both the capital and operating costs associated with the succinic acid production plant.

It is therefore desirable to provide a process for the production of dialkly succinate from bio-succinic acid without the need for the complex and expensive purification steps.

JP1216958 describes a process for the esterification of succinic acid using a homogeneous acid catalyst. In this process, an extremely dilute solution of the succinic acid in methanol is supplied, with a homogeneous catalyst to the upper region of a distillation column where it is passed in counter-current to methanol added at the base of the column. Esterification occurs within the column and the dialkyl succinate is removed from the base of the column. As a very dilute solution of the succinic acid is used, about 1 to 20 wt percent, a large methanol recycle flow will be required and substantial costs will be incurred in separating the methanol from the water of esterification produced in the reaction. Example 1 of JP 1216958 illustrated the problems associated with the deactivation of a resin catalyst where the succinic acid is bio-succinic acid.

The problems associated with using bio-succinic acid in an esterification reaction in the presence of a resin catalyst are also illustrated in Example 1 of *"Reaction Kinetics for the Heterogeneously Catalyzed Esterification of Succinic Acid with Ethanol"* Kolah A K et al Ind. Eng. Chem. Res., 2008, 47(15) pp 5313-5317, *"Pervaporation-assisted Esterification of Lactic and Succinic Acids with Downstream Ester Recovery"* Benedict et al, J. Membrane Sci., 2006, 281 pp 535-445, *"Combined Technology of Catalytic Esterification and Absorption of Succinic Acid"* Ding B et al The Chinese Journal of Process Engineering 2007-01, U.S. Pat. No. 5,723,639, and *"Preparation of Diethyl Succinate by Catalytic Esterification and Absorption Dehydration"* Gang C et al China Surfactant Detergent & Cosmetics 2008-04.

Various processes have been suggested for carrying out the esterification in a non-catalysed system.

In JP 04091055 succinic monoester obtained by the esterification reaction of succinic acid or succinic anhydride is introduced into a reactor with alcohol. The reaction to the diester is carried out in the absence of a catalyst. It is likely that the product removed from the bottom of the reactor will still contain significant amounts of mono-ester and as such would be unsuitable for use in downstream reactions using, for example, a copper catalyst. In addition, it is believed that the diester taken from the base of the reactor will include heavy impurities carried over from the production of the bio-succinic acid.

A further problem with non-catalysed reactions is that these systems are likely to have a low conversion rate and will therefore have a high acid content. Since many of the known processes for producing, for example, 1,4-butanediol use a copper based catalyst, the presence of the acid is problematic since it will be deactivated by the acidic species present. This will necessitate regular shut down to replace the deactivated catalyst. This deactivation may be exacerbated in systems where the starting material includes a double bond due to the high heat release on the conversion of the double bond in the hydrogenation step. To address this, the acid would have to be removed, which would require a number of steps which would add to the capital and operating costs of the process.

Using dialkyl succinate may overcome the problems associated with the high heat released on the conversion of the double bond and offer various other advantages such as obviating the risks of fumarates being formed which is also a problem associated with using maleic anhydride as a starting material. However, if the di-esterification of the succinic acid is not complete, acidic species will still be present in the reaction feed which can lead to deactivation of the catalyst unless steps are taken to remove the acid. It is therefore desirable to have a process which produces complete conversion to the di-ester and in particular a di-ester which is a suitable feed to a hydrogenation reaction. High conversion will require a large excess of dry alkanol. The recovery and recycle of this dry alkanol incurs high capital and operating costs.

There are also problems associated with using succinic acid as the starting material. Succinic acid is a crystalline solid at ambient temperatures and has a melting point above normal esterification temperatures. In addition it has low solubility in water and alkanols such as methanol. These limit the manner in which it can be used. This presents challenges in using succinic acid as a starting material in conventional esterification processes which are generally tailored to liquid feeds.

A further problem is that the volatility of the dialkyl succinate means that although in conventional counter-current reactions, the diester is predominately removed from the base of the column, a portion will carry over from the top of the reaction column with the produced water of esterification and excess alkanol and will be lost thereby reducing the efficiency and hence impacting on the economics of the process. In addition, the presence of the ester in this stream can create an effluent problem.

It is therefore desirable to provide a process which addresses at least some of the above-identified problems which occur when the starting material is bio-succinic acid. It is particularly desirable to provide a process which addresses all of the above problems.

The problem may be addressed by carrying out an auto-catalytic reaction in a reaction distillation zone column in which the acid and the alcohol flow co-currently in an esterification reaction column, recovering a stream comprising the ester from the column and purging the heavy impurities from at or near the base of the column. A combination of distillation and phase separation and stages can enable the prior art problems to be addressed.

Thus according to the present invention, there is provided a process for the production of dialkyl succinate from a bio-succinic acid feedstock comprising the steps of:
 (a) feeding bio-succinic acid to a point at or near the bottom of a reaction distillation zone column operated at temperatures and pressures to enable esterification of the succinic acid and passing said stream co-currently with upflowing alkanol such that said esterification reaction occurs;
 (b) removing an overhead vapour stream from at or near the top of the reaction distillation zone column comprising di-ester, alkanol, water of esterification and organic components and passing said stream to an alkanol separation column where the alkanol is separated from the water of esterification and from the organic components;
 (c) removing a side draw from the alkanol separation column from a point below the feed point thereto, said side draw comprising partially immiscible organic and aqueous phases;
 (d) passing said side draw to phase separation apparatus where the partially immiscible organic and aqueous phases are separated;
 (e) passing said organic phase to a column where the dialkyl succinate is separated from residual water and other organic components; and
 (f) recovering the dialkyl succinate.

By removing the di-ester at or near the top of the reaction distillation zone column, the problems associated with the heavy impurities from the feed contaminating the ester, which are noted where the product is taken from the bottom of the column as occurs in counter-current systems, are overcome. Further, carrying out the reaction and initial distillation in a co-current manner enables unreacted acid and mono-ester to be retained within the column by internal recycles for subsequent reaction thereby improving the conversion and hence the efficiency of the reaction.

A further benefit of the present invention is that the ratio of alkanol required to complete the conversion to the diester is reduced when compared to that required for counter-current reactions. In the counter-current systems, where the succinic acid is introduced slurried or dissolved in methanol, a significant proportion of that methanol flashes into the vapour phase and therefore does not take part in the liquid phase reactions. In contrast, in the present invention, where the reaction column is operated in a co-current manner, all of the alkanol is available for the esterification reaction. As the ratio of alkanol to the succinic acid is lower in the present invention, the size of reactor vessels can be reduced and hence the capital and operating costs are similarly reduced. In addition, energy requirements will be reduced.

The feed to the reaction distillation zone column will comprise bio-succinic acid which will include the impurities which are present following the formation of the succinic acid by fermentation of biomass. Impurities present will depend on the source of the biomass and the fermentation process employed. However, they will generally include one of more of proteins, sugars, amino acids, succinamic acid, succinamides, ammonium, sulphur, organics and metal ions. Organics include other organic acids such as acetic acid, pyruvic acid, fumaric acid, malic acid and/or lactic acid. The metal ions may be present in the biomass due to nutrient or feed impurities. The present invention enables the reaction to be carried out without the requirement to separate out these impurities in advance of the esterification reaction.

In one arrangement, the bio-succinic acid may be supplied to the reaction distillation zone column as a solid. In another arrangement, it may be provided as a slurry or in solution in alkanol or water. Where it is provided as a slurry or solution in alkanol, this alkanol may represent the full alkanol inventory or a part thereof. Where it is only a part of the full requirement, make-up alkanol may be added to the reaction distillation zone. The overall ratio of alkanol to succinic acid will be in the region of about 3:1 to about 10:1. It will be understood that this is above the stoichiometric ratio for the esterification of succinic acid.

The present invention may be operated with bio-succinic acid feed comprising 50 wt % or more succinic acid. In one arrangement, it may be 80 wt % or more. The acid feeds may include up to about 20 wt % water. However, a lower water content is generally preferred. The water content will vary with the crystallisation conditions and drying profile. In one arrangement, the typical water content will be in the region of about 5 wt % water. The remainder will generally be the impurities.

The bio-succinic acid feed may be co-fed with one or more of maleic acid, maleic anhydride and mono-alkyl maleate.

The reaction distillation zone column operates in co-current manner and as the di-ester of succinic acid is more volatile than both the succinic acid and the mono-ester it is preferentially vaporised from each reaction stage, and therefore its concentration upwardly through the column will increase. The temperature profile can be designed to retain the acid and mono-ester in the column until di-esterification has occurred. Thus the conversion to the desired product is optimised.

In one optional arrangement, before the bio-succinic acid is added to the reaction column, it may be pre-reacted with alkanol in a pre-reactor. Suitable pre-reactors include a stirred tank reactor. The stirred tank reactor is preferably a continuous stirred tank reactor. Any suitable reaction conditions may be operated. In one arrangement the stirred tank reactor will be operated at a temperature in the region of from about 120° C. to about 140° C. to enable the crystals of succinic acid to be dissolved and to keep the acid in solution and to allow the esterification reaction to occur. Suitable temperatures include 120° C., 125° C., 130° C., 135° C. and 140° C. The pressure within the stirred tank reactor may be in the region of from about 5 bara to about 10 bara. This is the optimum pressure to keep the alkanol in solution. Suitable pressures include 5 bara, 6 bara, 7 bara, 8 bara, 9 bara and 10 bare. Where an elevated pressure is used, the first reactor will be operated at a sufficiently high temperature for the autocatalytic esterification reaction to proceed relatively fast, in the order of 20 to 90 minutes, and the vaporisation of the alkanol to be prevented. The vaporisation is undesirable as it will adversely affect the reaction equilibrium. In one arrangement, the reaction time will be of the order of 40 to 50 minutes.

Any suitable molar ratio of alkanol to succinic acid may be selected for the stirred tank reactor. In one arrangement, the molar ratio selected will be of from about 1:1 to about 6:1 alkanol to succinic acid. Molar ratios of about 2:1, 3:1 and 4:1 may also be used. It will be understood that increased alkanol will reduce reaction time. However, the presence of increased alkanol will increase the cost of alkanol recycle.

Heat may be generated in the autocatalytic reaction in the pre-reactor. A portion of this may be used to overcome the heat of dissolution of the bio-succinic acid where the feed is a solid or a slurry. Any residual heat may be recovered and utilised in the process of the present invention or in upstream or downstream reactions. This may be by means of condensing vapourised alkanol or my alternative means. In an alternative arrangement, heat may have to be supplied to overcome the heat of dissolution.

The stream removed from the pre-reactor may be a solution but may contain some residual solids. In one arrangement, the stream removed from the pre-reactor may be a slurry.

The product stream from the pre-reactor comprising unreacted succinic acid, mono alkyl ester, dialkyl ester, alkanol, water of esterification and impurities may optionally be passed via a subsequent reaction vessel where further reaction occurs such that the conversion of any mono-ester to di-ester is increased. Any suitable subsequent reaction vessel may be used. In one arrangement, a plug flow reaction vessel may be used. Any suitable reaction conditions may be used in this reactor which allows the further esterification to occur.

If the subsequent reaction vessel is used, the reaction stream recovered from the plug flow reactor will be passed to the reaction distillation zone column.

Where a pre-reactor, optionally with a subsequent reactor are used, the recovered steam may be treated such that there is a crude removal of the water of esterification, and optionally, excess alkanol. Any suitable treatment means may be provided. In one arrangement, a flash/distillation column may be used.

Additionally or alternatively, the temperature of the reaction stream may be adjusted as required before being added to the reaction distillation zone column.

The use of the optional pre-reactor and the optional subsequent reaction vessel will generally reduce the amount of alkanol required for the reaction distillation zone column.

Any suitable reaction distillation zone column arrangement may be used. In general it will be designed to maximise reaction and improve separation. Thus a plurality of reaction distillation stages may be used. In one arrangement, the reaction distillation zone column will comprise liquid hold-up trays to afford extra residence time therein. In addition, conventional distillation stages may be located in the reaction distillation zone column above the reactive distillation stages. By this arrangement, heavy impurities, succinic acid and mono-ester can be retained in the reaction distillation zone column. A partial condenser may be present to assist in retaining the impurities in the column. The heavy impurities may then be purged from the sump of the reactor.

In one alternative arrangement, a divided wall column may be used. In this arrangement, the feed may be fed to opposite sides of the wall to any recycles.

The reaction distillation zone column may be operated at any suitable reaction conditions to assist the furtherance of the reaction. An overheads pressure of about 1.3 bara to about 10 bara. Pressures of 1 bara, 2 bara, 3 bare, 4 bara, 5 bara and 6 bara may be used. A pressure of about 2 bara may offer certain advantages particularly where the alkanol is methanol. The pressure is selected to allow sufficient alkanol concentration to be retained in the liquid phase at the required reaction temperature.

Any suitable reaction temperature may be used. In one arrangement the reaction distillation zone column may operate at a temperature of about 80° C. to about 300° C. Particular advantages may be noted where a temperature of about 100° C. to about 200° C. is used. A temperature of about 150° C. may be particularly advantageous. The temperature in the column sump may be about 80° C. to about 250° C. while the temperature in the overheads of the column may be about 80° C. to about 170° C.

The reaction in the reaction distillation zone column may be carried out in the absence of a catalyst such that it is auto-catalysed. In an alternative arrangement, a catalyst may be used. In one arrangement, the catalyst may be located in the sump of the reaction distillation zone column. In an alternative arrangement, the catalyst may be located in the upper stages of the reaction distillation zone column. By this means, the impurities will not come into contact with the catalyst.

The stream removed from at or near the top of the reaction distillation zone column is passed to an alkanol separation column. In one alternative, before the stream is passed to the alkanol separation column, it may be passed through a condenser, or part condenser, to recover heat which may be used in the system. In addition, this will reduce the cooling water load on any condenser on the alkanol separation column. Fully condensing the overheads stream may be desirable to allow the reaction distillation zone column to operate at a lower pressure, rather than a higher pressure, than the alkanol separation zone in order to moderate the temperature of the sump of the reaction distillation zone column. This will allow lower grade reboil heat and hence allow lower grade material to be used for construction. In one arrangement, the presence of the alkanol separation column can give an overhead pressure of about 1.3 bara.

The stream removed from the reaction distillation zone column may be supplied to any suitable point of the alkanol separation column. In one arrangement it will be supplied at or near a central region thereof.

The alkanol separation column may be of any suitable configuration. Alkanol will be removed from at, or near to, the top of the alkanol separation column. This alkanol may be recycled to the reaction distillation zone column and/or to the pre-reactor where present. Conventionally, this alkanol will be removed as a liquid. In one arrangement, the alkanol may be removed as a vapour. Generally the vapour will be compressed before being pumped to the point at which it will be used. By this means, the condenser duty on the alkanol separation column can be reduced. Where the vapour is returned to the reaction column, having it as a vapour will reduce the vaporisation duty for the reboiler of the reaction column.

In one arrangement, a purge may be taken. This purge may remove light impurities and/or sulphur. As the alkanol is continuously removed overhead from the reaction distillation zone column, the reaction is not equilibrium limited and as such very high purity alkanol is not required to achieve a high purity di-ester product. The alkanol separation column will be operated at any suitable conditions to enable the separation to occur. In one arrangement, the pressure of the column overhead will be in the region of about 1.3 bare to about 2 bara. This is particularly appropriate where the alkanol is methanol. Pressures of about 1.5 bara, about 1 bara, and about 1.5 bara. The temperature will depend on the alkanol used. Where the alkanol is methanol, the temperature will be about 70° C.

A stream comprising the desired di-ester is removed from the alkanol separation column as a side draw. Generally, the side draw is removed from the alkanol separation column at a point below the feed point. As this side draw comprises partially immiscible organic and aqueous phases, it is passed to a phase separation apparatus. Any suitable phase separation apparatus may be used. In one arrangement, a decanter may be used.

The feed to the phase separation apparatus may be cooled to enhance the phase separation.

In one arrangement, the separated aqueous phase is returned to the alkanol separation column. The returned aqueous phase is generally returned to a point below the draw point. In a preferred arrangement, the aqueous phase is added just below the draw point. This will allow the water/dialkyl succinate azeotrope to be overcome and will minimise di-ester slippage into the alkanol separation column bottoms. An interchanger may be used to recover heat from the aqueous phase being returned to the alkanol separation column.

The organic phase recovered from that of the phase separation apparatus may be passed to the reaction distillation zone column. In this arrangement, a stream removing liquid dialkyl succinate will generally be removed from the reaction column as a side draw below the point at which the organic stream from the phase separation apparatus is supplied to the reaction distillation column. In this arrangement, a purge may be taken from the alkanol separation column to remove butanol. The purge may be taken from a point below the feed point but above the dialkyl succinate/water draw. The draw may be passed through the decanter to minimise the water/alkanol/dialkyl succinate losses in the purge.

In an alternative arrangement, the organic phase recovered from the phase separation apparatus may be passed to a dialkyl succinate separation column. This column preferably operates at mild vacuum to moderate the temperatures required. In one arrangement, the pressure of the column overhead will be in the region of about 0.1 bara to about 1 bara. Pressures of about 0.25 bara, 0.5 bara and about 0.75 bara. The bottoms from the column will be essentially 100% dimethylsuccinate and thus the temperature will be about 140° C. to about 170° C. depending on the operating pressure.

Generally the di-alkyl succinate will be removed from the dialkyl succinate separation column as a bottom stream.

In one arrangement, any residual water in the feed to the dialkyl succinate separation column is removed as an overhead. It may be recycled to the alkanol separation column.

Streams containing water from downstream reactions, such as those from the distillation train in the butanediol production process, may be fed to the alkanol separation column. Where this occurs, butanol, which is a by-product of the hydrogenolysis reaction in the production of butanediol, will concentrate in the organics phase from the phase separation apparatus and may optionally be purged from the dialkyl succinate separation column, generally as a liquid draw. Additionally or alternatively, butanol may be purged from the alkanol separation column.

This butanol purge, if taken, may contain a significant portion of dialkyl succinate which will be a loss to the system. In one arrangement, these losses may be reduced by replacing the liquid draw purge and allowing more organics to pass into the overhead stream. In this arrangement, the overhead is passed to a second phase separation apparatus where the aqueous phase is separated from the organic phase. This second phase separation apparatus may be a decanter. In one arrangement, the aqueous phase may be returned to the alkanol separation column. It may be supplied directly to the alkanol separation column or it may be combined with the aqueous phase from the phase separation apparatus located after the alkanol separation column.

In one arrangement, the organic phase from the second phase separation apparatus is passed to a dialkyl succinate/butanol separation column. In this arrangement, butanol is concentrated in the overheads of the dialkyl succinate/butanol separation column and a high purity di-alkyl succinate stream is recovered from at, or near, the column bottoms.

As the feed to the dialkyl succinate/butanol separation column will generally be of relatively low volume, the dialkyl succinate/butanol separation column may advantageously be arranged as a side column in the dialkyl succinate separation column. In this arrangement a vapour draw from the bottom of the dialkyl succinate separation column may be used in place of a dedicated reboiler.

In one alternative, the dialkyl succinate/butanol separation column and the dialkyl succinate separation column may be integrated by the use of a divided wall at the base of the dialkyl succinate separation column.

In an alternative arrangement, a portion of the diester produced in the reaction distillation column zone is removed as a liquid side draw. The remainder is removed in the overhead and passed to the alkanol separation column as discussed above. In one arrangement, a major portion of the diester is removed in the side draw. In this arrangement, the reflux ratio of the reaction distillation zone column will generally be increased so that the majority of the separation of the dialkyl-succinate from the water of esterification and excess methanol occurs within the reaction distillation zone column rather than in the alkanol separation column.

A portion of the hot dialkyl ester draw from the reaction distillation zone column may optionally be supplied to the dialkyl succinate separation column where the vapour flashed by letting down the pressure can be used in place of a reboiler on the column.

Where a portion of the product stream is removed as a side draw from the reaction distillation column and where aqueous recycle streams from the downstream distillation train of butandiol production, the butanol which is a by-product of the hydrogenolysis reaction may be optionally purged as a liquid draw from the alkanol separation column rather than the dialkyl succinate separation column since the dialkyl succinate concentration is lower and thus di-ester losses are reduced.

The esterification in the reaction distillation zone column and one or both of the alkanol separation and the dialkyl succinate separation can be performed in separate columns. In one alternative, the reaction distillation column zone and one or both of the distillation columns can be combined in a single column. In this latter arrangement, the unreacted acid and mono-ester are largely retained in the reaction distillation column zone by the column reflux with only the more volatile ester leaving overhead. A benefit of keeping the reaction and distillation zones in a single column has the benefit of keeping the recycles within the column.

Certain advantages may be noted where the reaction distillation zone column and the alkanol separation and the dialkyl succinate separation columns are located in separate columns since the column overhead pressures can be tailored to the specific requirements of the respective column.

In some embodiments, where the composition of the sump in the reaction distillation zone column is largely succinic acid and monoalkyl succinate, a high temperature, possibly in the region of 240° C. or above, may be noted. This high temperature may provide some challenges. First, substantial heat may have to be provided to the reboiler. This may be of the order of 40 bar steam. Further, the corrosive nature of the compositions present in the reactor at these temperatures may mean that higher grade materials may be required for the fabrication of the reactors. It is also possible that at these temperatures by-product reactions may occur and/or thermal decomposition of feedstock impurities may become significant which will negatively impact on the efficiency of the reaction. It is therefore desirable to seek to mitigate these challenges in the embodiments where they occur.

In arrangements where this occurs, it may be desirable to remove a purge from the sump of the reaction distillation zone column. The purge may be taken at a higher than conventional rate. A purge up to about 5% of the feed rate may be taken. This purge may optionally be mixed with alkanol and passed to a purge reactor in which succinic acid and monoalkyl succinate are converted to the desired dialkyl succinate. This dialkyl succinate may be directly recovered, or in one arrangement may be recycled to the reaction distillation zone column. Where the dialkyl succinate is returned to the reaction distillation zone column, it will generally be supplied above the reaction stages of the column.

The alkanol mixed with the purge will generally be provided in a large excess. In one arrangement 4 or 5 moles of alkanol may be used for each mole of succinic acid and monoalkyl succinate.

Any suitable reactor may be used for the purge reactor. In one arrangement, the reactor will be a plug flow type reactor. Any suitable reaction conditions may be used for the purge reactor. Generally, the purge reactor will be operated at a higher pressure, normally 10 to 20 bara, than the column in order to keep the alkanol in solution at sufficiently high temperatures for conversion to occur. Suitable temperatures include about 150° C. to about 180° C. Whilst a catalyst may be used, generally the reaction will be autocatalytic. The residence time may be from about 1.5 to about 2 hours. It is believed that this should allow 75% or more of the succinic acid and monoalkyl succinate in the purge stream to be converted. This would allow the reaction distillation column zone sump temperature to be reduced to about 220° C.

Any suitable alkanol may be used. Generally a $C_1$ to $C_4$ alkanol will be used with methanol or ethanol being preferred and with methanol being particularly preferred.

As the process of the present invention can utilise succinic acid of a lower purity such as bio-succinic acid, there are significant savings in the number of purification steps required to be performed on the product of the fermentation process. Thus the costs will be substantially reduced and the succinic esterification plant will be able to supply feed to the butanediol plant at a competitive price in comparison to the conventional maleic anhydride.

In one arrangement, a weak base anion exchange resin system may be used as a polishing step to remove any residual impurities which may be present and which could poison any catalyst used in downstream reactions. This polishing step will also act as a guard bed to protect downstream catalyst in the event of slippages in the operation of the present invention. In one arrangement the exchange resin could be a sacrificial system in which case it will generally be constructed for ease of replacement. In an alternative arrangement, it will include a regeneration system with a base solution.

The condensing requirement for the alkanol may be reduced by using mechanical vapour re-compression of any alkanol recycle stream such that it can be introduced directly into the bottom of the reaction distillation zone column.

Whilst the present invention has been described with reference to a purpose-built plant, it will be understood that conventional plants, such as those built to operate the processes described in U.S. Pat. No. 479,584 and WO 90/08127, may be adapted to use the present invention.

The dialkl succinate produced in the present invention may be used in the production of 1,4-butanediol, tetrahydrofuran and/or γ-butyrolactone. In addition, it may be used in other processes such as in the manufacture of pharmaceuticals, agrochemicals, perfumery products, plastics, coatings, dyes, pigments, printing inks and other organic compounds. Further it may be hydrolysed back to succinic acid. In this case, the acid will have a higher purity than the acid fed to the present invention.

The present invention will now be described by way of example with reference to the accompanying drawings in which:

FIG. 4 is a schematic illustration of a flow sheet according to a third aspect of the present invention;

FIG. 5 is an illustration of one design of a reaction distillation zone column suitable for use in the flow sheet of FIG. 2 or 3;

FIG. 6 is an illustration of a design of a reaction distillation zone column suitable for use in the flow sheet of FIG. 1, 4 or 7;

FIG. 7 is a schematic illustration of a flow sheet according to a fourth aspect of the present invention;

Figure 8A:
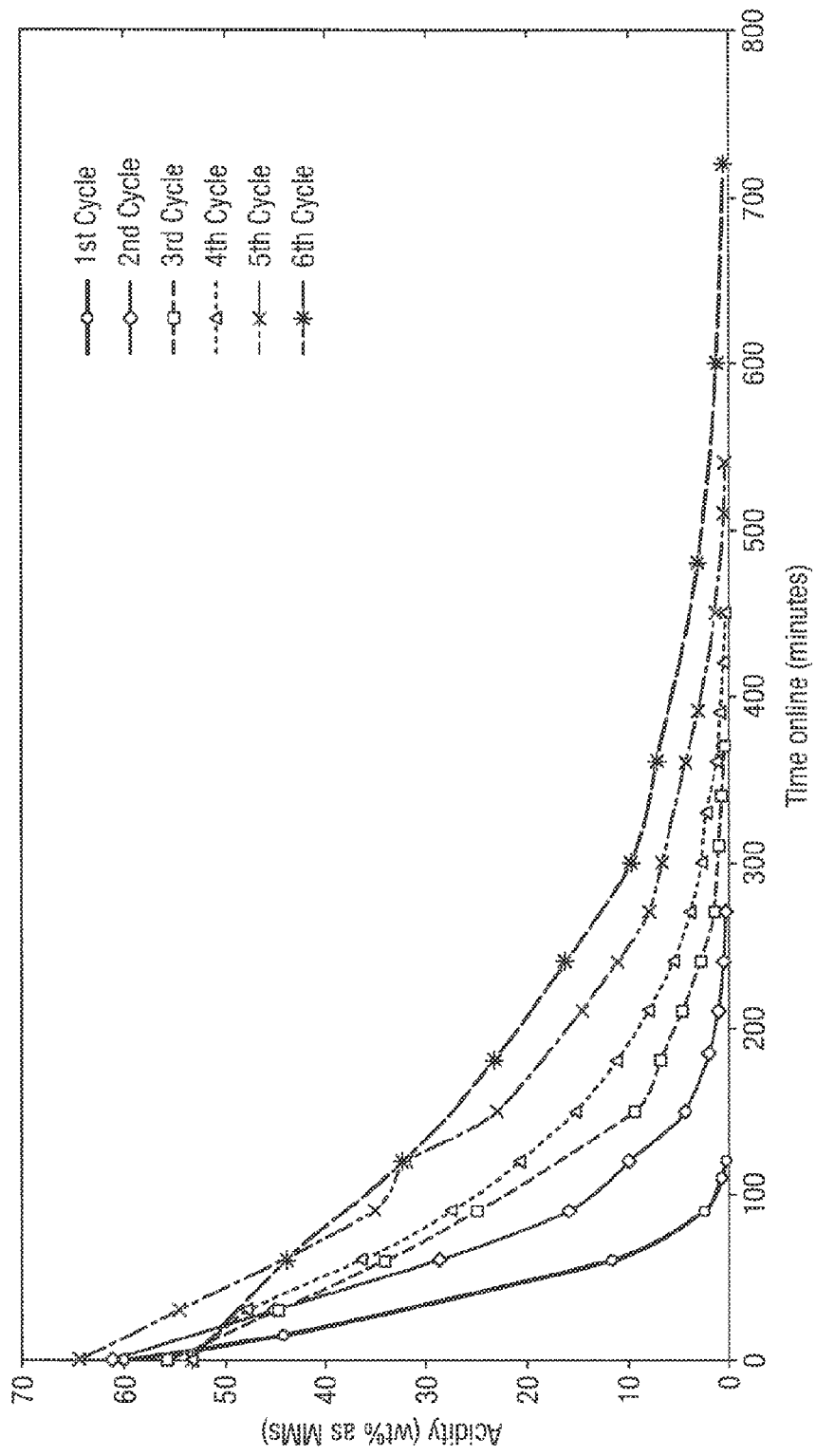
Figure 8B:
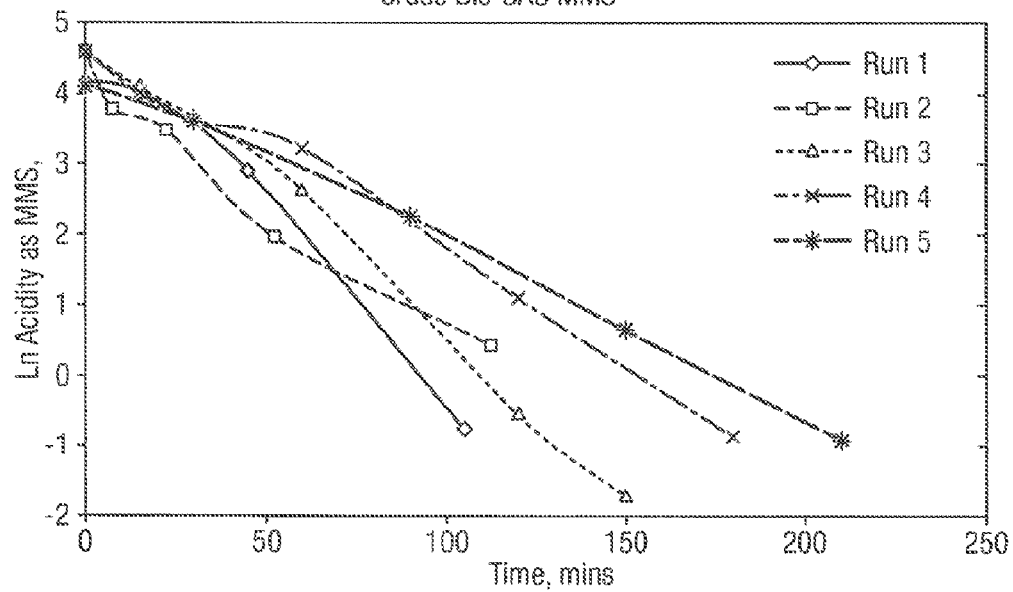
Figure 9:
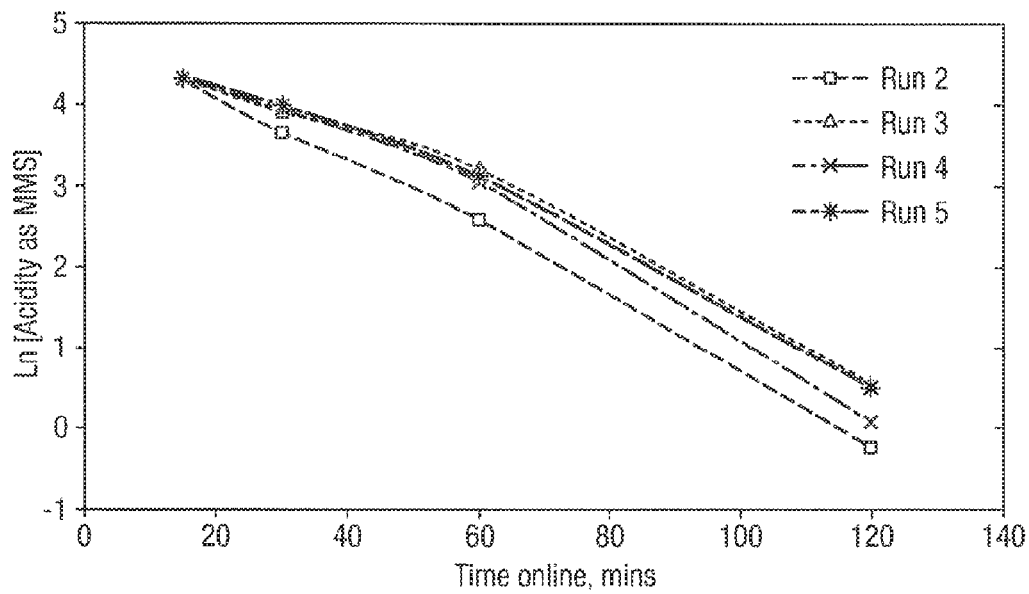
Figure 10:
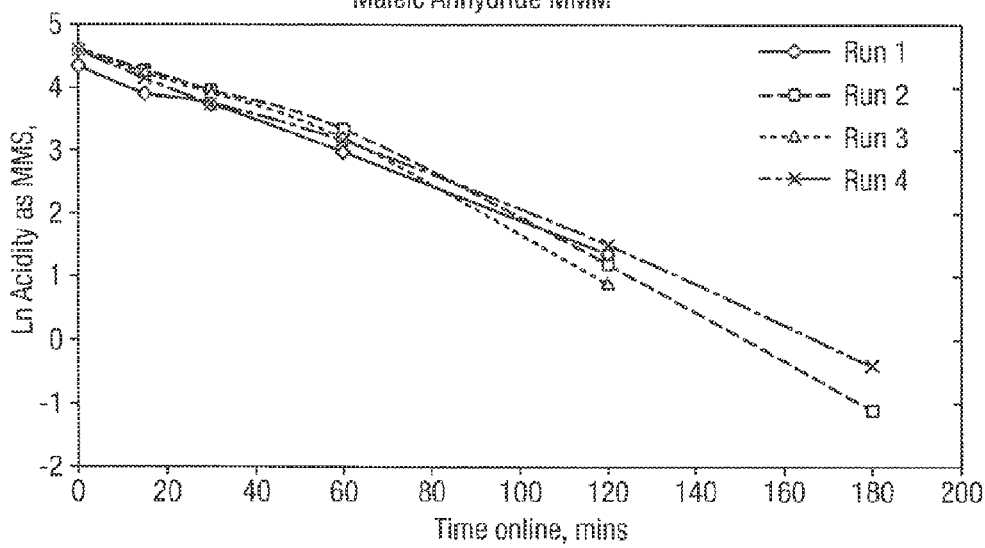
Figure 11:
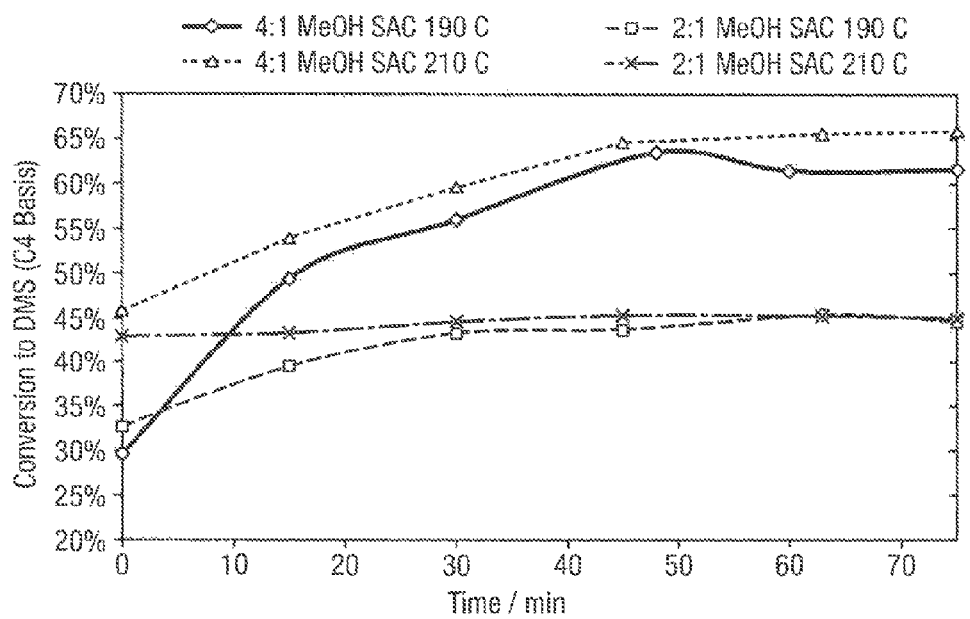
Figure 12:
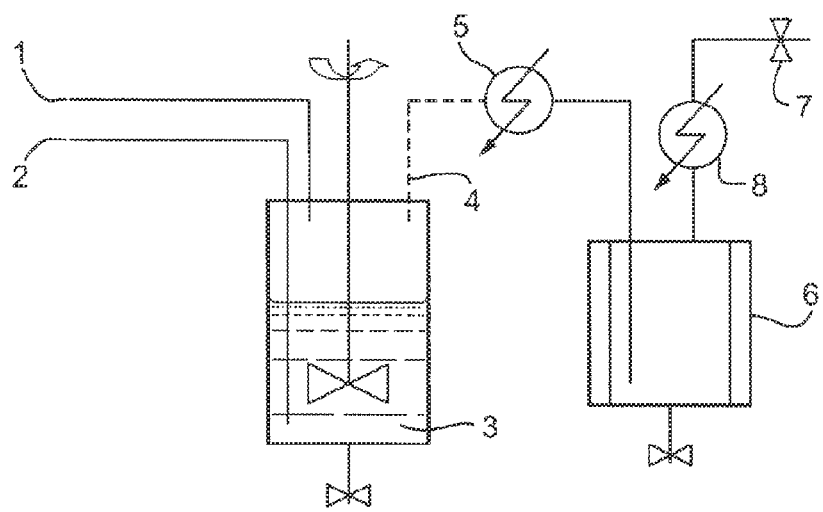
Figure 13:
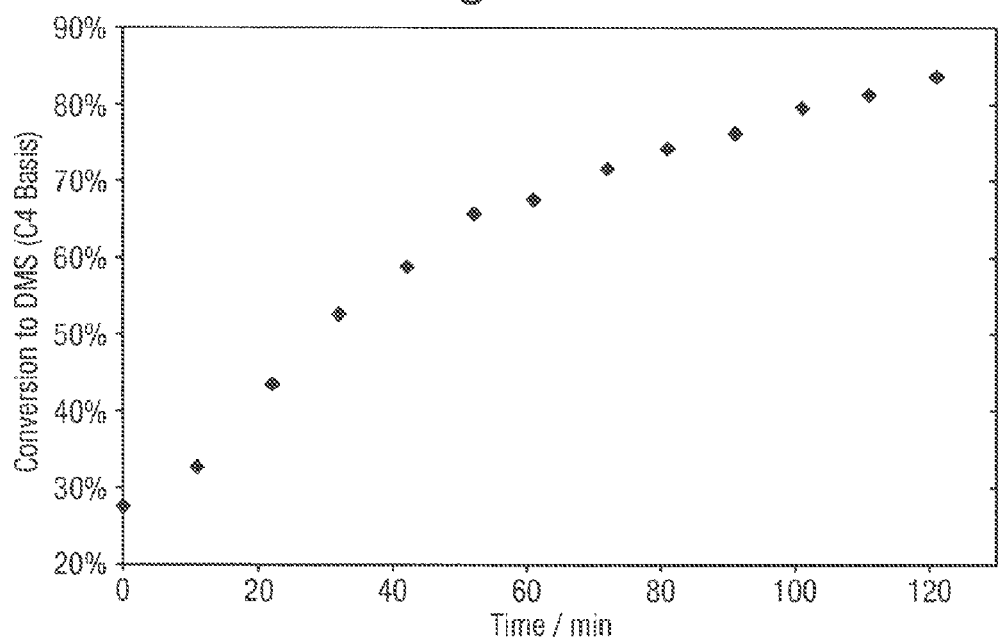
Figure 14:
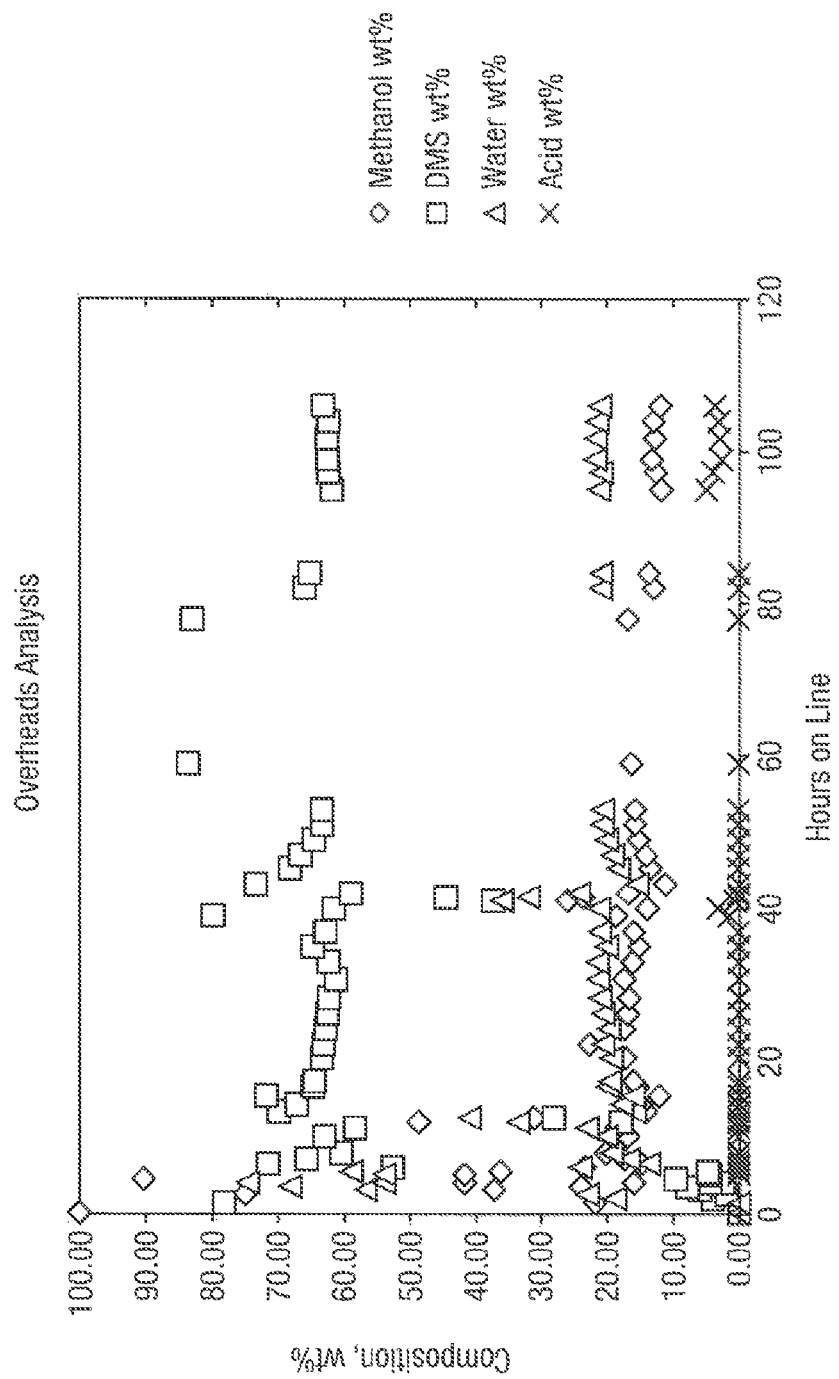

FIG. 8 is a graph of results from Background Example 1;
FIG. 9 is a graph of results from Background Example 2;
FIG. 10 is a graph of results from Background Example 3;

FIG. 11 is a graph illustrating the results from Example 1;
FIG. 12 is schematic representation of the autoclave set up used in Example 2;

FIG. 13 is a graph illustrating the results of Example 2 (run 1);
FIG. 14 illustrates the overheads analysis of Example 4;
FIG. 15 illustrates the flask analysis of Example 4;
FIG. 16 illustrates the temperatures of Example 4;
FIG. 17 illustrates the overheads analysis of Example 5;
FIG. 18 illustrates the pot analysis of Example 5; and
FIG. 19 illustrates the temperatures of Example 5.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

The invention will be discussed with reference to the methylation of succinic acid. However, it is equally applicable to the use of other alkanols.

Figure 1:
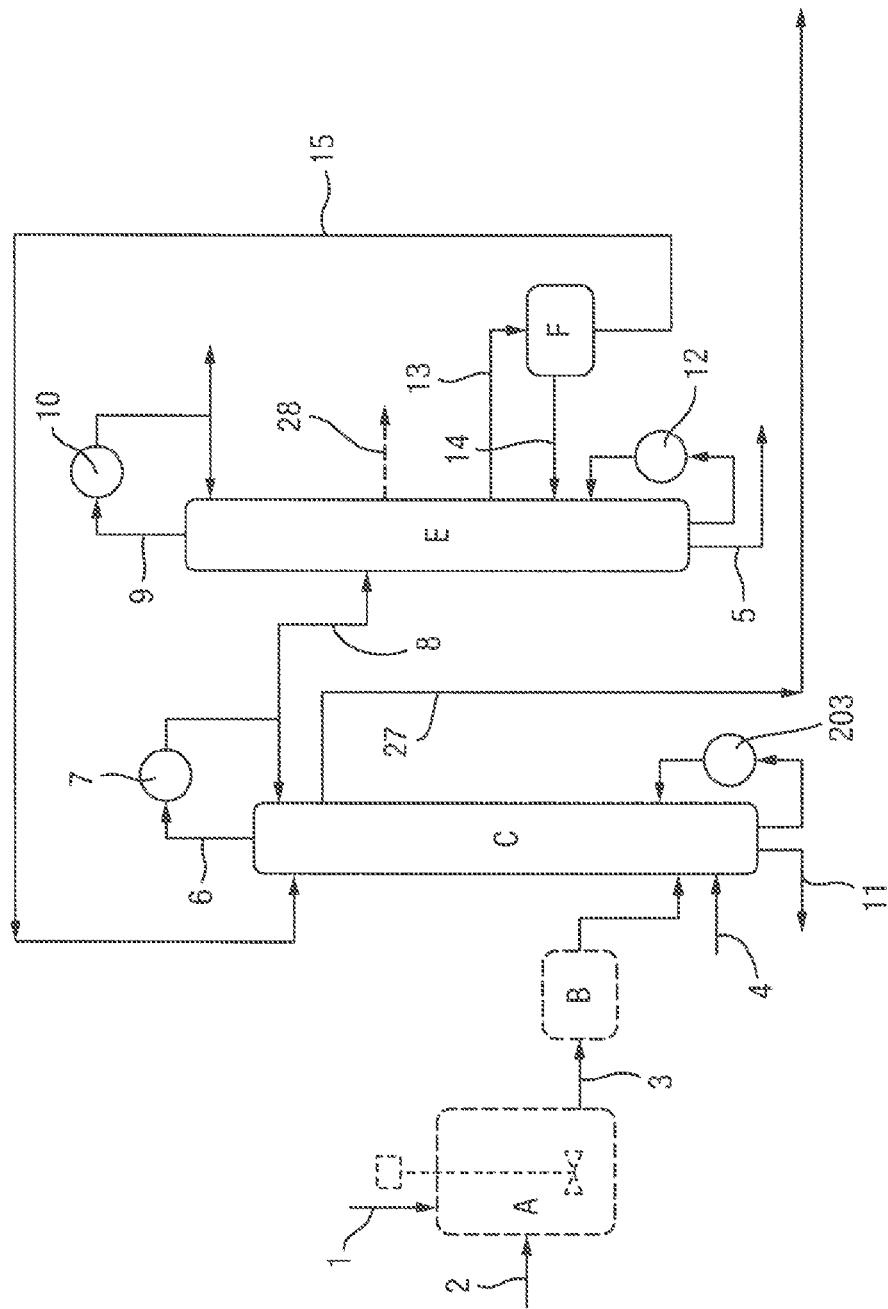
FIG. 1 is a schematic illustration of a flow sheet according to one aspect of the present invention.

As illustrated in FIG. 1, optionally, succinic acid crystals are added in line 1 to a continuous stirred tank reactor A operating at above atmospheric pressure by means of a lock hopper system. Methanol is added in line 2. The succinic acid is simultaneously dissolved in and reacted with the methanol. A product stream 3 from the continuous stirred tank reactor A comprises a part converted mixture of dissolved succinic acid, mono-ester, di-ester, methanol and water. This is optionally passed to a plug flow reaction vessel B where further conversion from mono to di-ester occurs. This feed is then passed to the distillation reaction distillation zone column C at or near the base thereof.

Alternatively, the succinic acid is fed directly at or near to the base of the reaction distillation zone column C. It may be fed as a solid or it may be pre-slurried in methanol. Where the plug flow reaction vessel B is admitted, the product stream 3 from the stirred tank reactor is fed directly to the reaction distillation zone column C. The succinic acid and reaction products will flow upwardly as vapour. Additional methanol may be added in line 4.

One example of a suitable arrangement for the reaction distillation column zone is illustrated in FIG. 6. In one arrangement, a distillation zone 202 is located above a reaction zone 201. Any suitable packing may be used for these zones. Trays of any suitable configuration may be used. A purge 11 is removed from the bottom of the reactor C. This will contain the heavy impurities from the bio-succinic acid. A portion of the purge may be returned through the reactor C via heater 203.

The bio-succinic acid and the methanol flow upwardly through the reaction distillation column zone C of FIG. 1. A methanol wash may be applied to the reaction zone column. Impurities from the feed are purged in line 11.

A stream comprising dialkyl succinate, water, and excess methanol are removed as an overhead stream 6. A condenser 7 may be provided to provide reflux. The remainder of the stream may be passed through an optional condenser G (illustrated in FIG. 2) to fully condense the stream before it is passed in line 8 to the alkanol separation column E. Fully condensing the stream enables the reaction distillation zone column to be operated at a lower pressure than the alkanol separation column.

A methanol stream is removed in line 29. A condenser 10 may be provided to provide column reflux. Column bottoms are purged in line 5. A reboiler 12 may be provided on the column E.

Butanol may be removed as a side draw in line 28 as shown in FIG. 1.

Dimethyl succinate is removed from the alkanol separation column E as a liquid side draw 13 from a point below the point at which line 8 is added to the column E. This stream 13, which will also include water, is passed to decanter F where the partially immiscible organic and aqueous phases are separated. The aqueous phase is returned to column E in line 14 to a point just below the point at which line 13 is removed. This allows the azeotrope between the water and ester to be overcome and minimise slippage of desired ester into the column bottoms.

The dimethyl succinate organic stream is removed from the decanter F in line 15 and returned to the reaction distillation column zone C at a point above the reaction stages.

The product stream is removed from reaction distillation column zone C in line 27 at a point below where the dimethyl succinate organic stream in line 15 is added the reaction distillation column zone C.

Figure 2:
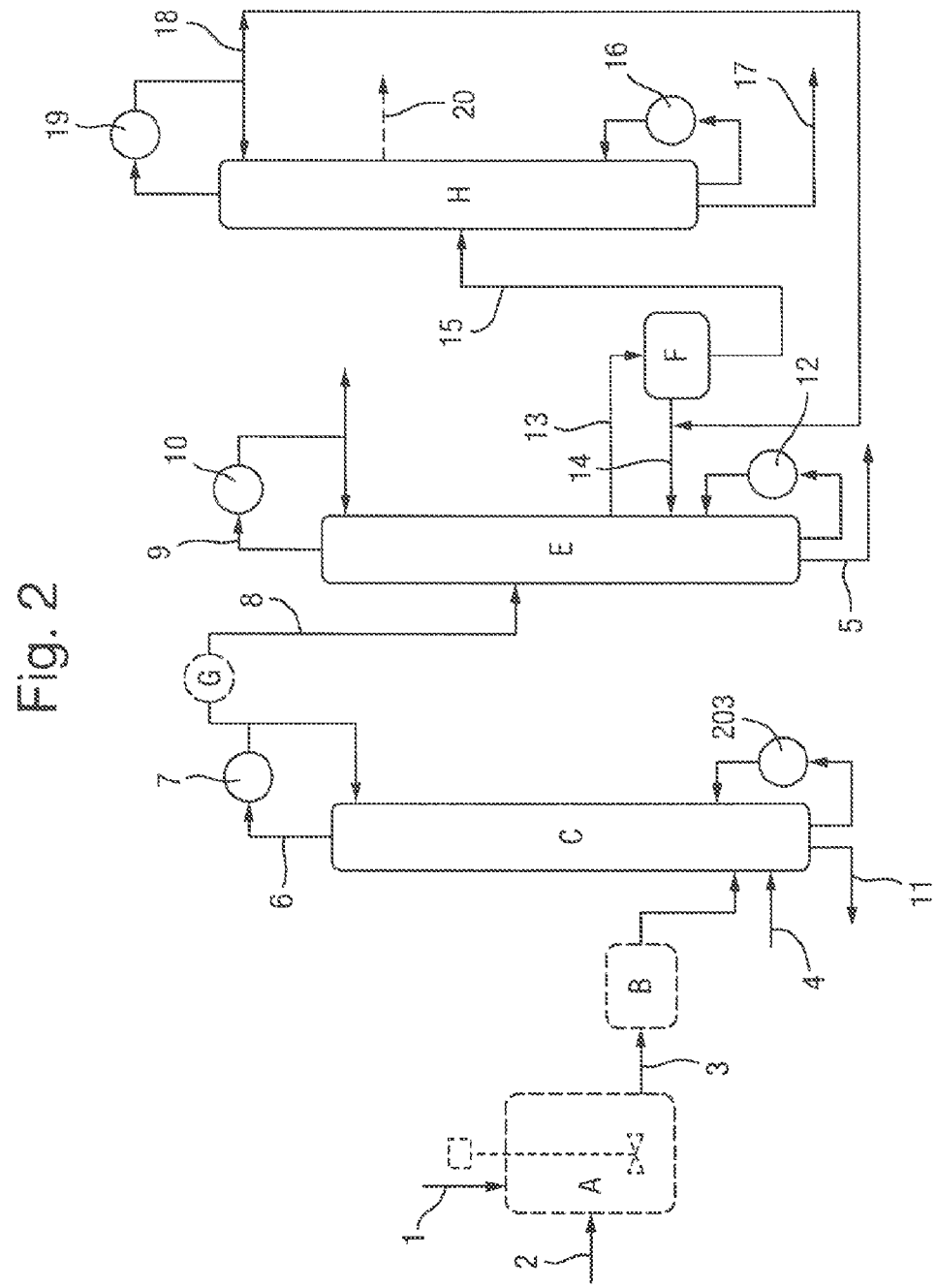
FIG. 2 is a schematic illustration of a flow sheet according to a second aspect of the present invention.

An alternative arrangement is illustrated in FIG. 2. In this arrangement, the dimethyl succinate organic stream removed from the decanter F in line 15 is passed to the dialkyl succinate separation column H. The column includes a reboiler 16. The dimethyl succinate product is recovered from column H in line 17. Any aqueous phase carried over in stream 15 from the decanter F will be separated in column H and will be removed overhead in line 18. This stream is recycled back to column E and will generally be added to the reactor with the aqueous stream 14 from the decanter F. A condenser 19 may provide column reflux.

Where the alkanol separation column is also used to separate streams containing water and methanol from a butanediol distillation process, butanol will concentrate in the organics phase in stream 15 from decanter F and may be purged from the dialkyl succinate separation column as a liquid draw in line 20.

Figure 3:
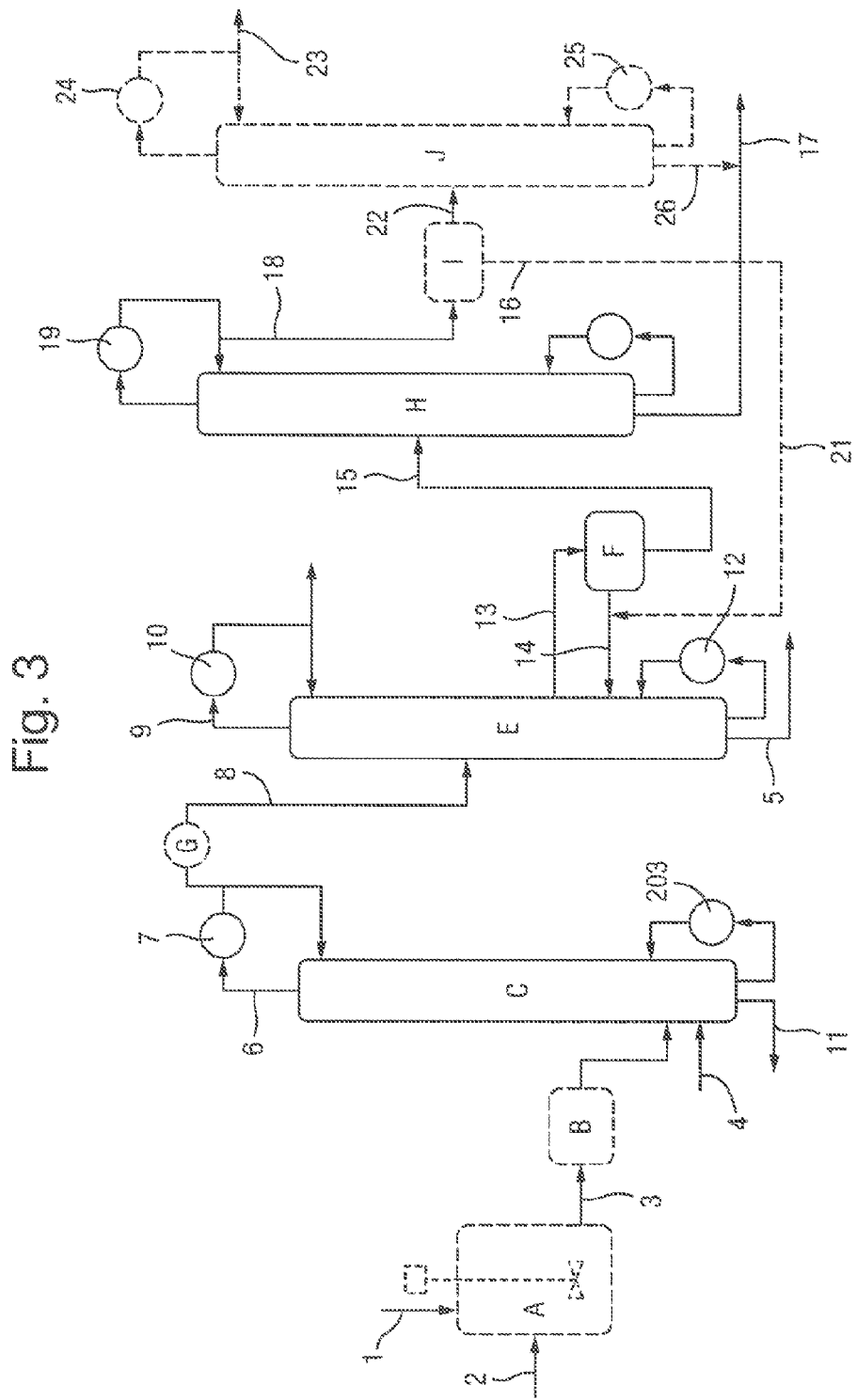
FIG. 3 is a schematic illustration of a modified arrangement of the flow sheet of FIG. 2.

A modified process is illustrated in FIG. 3. This is particularly suitable where the alkanol separation column is used to separate streams containing water and methanol from a butanediol distillation process. Although the arrangement described above in which the butanol is removed as a side draw in line 20 offers various advantages, some dialkyl succinate will be lost in this draw. The modified process, as illustrated in FIG. 3, addresses this.

In this arrangement, the side draw 20 is omitted and more organics are allowed to pass in line 18 to decanter I in which partially immiscible aqueous and organic phases are separated. The aqueous phase is returned to the alkanol separation column in line 21. The organic phase is passed in line 22 to a dialkyl succinate/butanol separation column J. Butanol is removed as overhead in line 23. A condenser 24 may provide column reflux. A column reboiler 25 will generally be provided. The dialkyl succinate is removed from the column J in line 26.

A further alternative to the arrangement of FIG. 2 is illustrated in FIG. 4. In this arrangement, a portion of the product is removed from reaction distillation zone column C as a side draw in line 27. Any butanol present can be removed as a side draw in line 28 from the alkanol separation column.

A schematic representation of a reaction distillation column zone C suitable for use in this alternative process is illustrated in FIG. 6.

A further alternative arrangement is illustrated in FIG. 7. This has been illustrated as a modification of the process illustrated in FIG. 1. However, it will be understood that this modification may be applied to any embodiment of the present invention.

A purge 30 is removed from the sample of reaction distillation zone column C and passed to a purge reactor K. The purge will generally comprise succinic acid and monomethyl succinate. This purge reactor is generally a plug flow type reactor. Methanol is added to the purge reactor K in line 31. The product from purge reactor K, which contains any unreacted components from the purge and of the desired dimethyl succinate are returned in line 32 to the reaction distillation zone column C.

The present invention will now be described with reference to the following examples.

BACKGROUND EXAMPLE 1

A 1 liter autoclave was charged with Myriant bio-succinic acid (500 g, 4.2 mol) and methanol (149 g, 4.7 mol, 1.1 equivalent). The vessel was sealed, pressurised to 40 bar(g) under nitrogen and heated to 200° C. at which point the reaction mixture was agitated by stirring at 300 rpm. After 3 hours the vessel was cooled and the product discharged as a light-brown slurry. This process was repeated until sufficient monomethyl succinate had been prepared for further esterification testwork.

The testwork was repeated to obtain discrete samples of monomethyl succinate derived from crude and pure Myriant bio-succinic acid samples.

A 500 ml reaction vessel was charged with 300 g of the crude bio-mono-methyl succinate and 30 g of DPT-2 resin (available from Johnson Matthey Davy Technologies Limited). The vessel was then heated to give an approximate pot temperature of 115° C., with the flange heated to a temperature of 120° C. to reduce internal reflux. Methanol was then introduced directly into the liquor at 3 molar equivalents per hour. The resulting vapour was removed and condensed. Samples of the liquor were taken with time and analysed by titration against 0.1 M potassium hydroxide using phenolphthalein as the indicator and acetone as the solvent. The reaction was continued until the monomethyl succinate concentration was <0.5 wt %.

The experiment was repeated to give 4 runs, the results of which can be seen in FIG. 8. The results of the testwork suggest that there was deactivation of the resin with the crude Myriant succinate.

Analysis of the deactivated resin by XRF indicated the presence of relatively large amounts of Fe, however, this was not seen in the crude bio-monomethyl succinate.

BACKGROUND EXAMPLE 2

The experiment described above was repeated using bio-monomethyl succinate derived from pure Myriant bio-succinic acid. Five repeat runs were performed using the same charge of ion exchange resin, the results of which can be seen in FIG. 9. The results indicate that there is little deactivation of the resin with the purer material.

BACKGROUND EXAMPLE 3

To confirm the efficacy of the experiments on the Myriant bio-succinic acid samples the process described above was repeated, for a mono-ester feed derived from maleic anhydride. To a 3-necked round-bottomed flask was added maleic anhydride (2 kg, 20.4 mol). The vessel was heated to 60° C. with stirring, at which point methanol (784 g, 3 mol equivalent) was added drop-wise, maintaining an exotherm of less than 10° C. Once the methanol addition was complete the vessel was crash cooled under running water and discharged.

Four repeat esterification tests were performed using the monomethyl maleate synthesised above according to the procedure described previously using the same sample of resin. There was no evidence of deactivation as illustrated in FIG. 10.

EXAMPLE 1

This example demonstrates esterification of succinic acid with methanol at temperatures of 190-210° C. in batch autoclaves.

Studies on succinic acid conversion were undertaken using 6×100 cm$^3$ Hastelloy™ autoclaves each containing a cross-shaped magnetic follower. Heating was provided by a metallic block-heater which was close-fitted to each autoclave. Heating was controlled by a suitable temperature controller and each autoclave was individually magnetically stirred. The block was pre-heated to the desired reaction temperature prior to the addition of the autoclaves.

Each autoclave was individually charged with the desired starting composition of succinic acid and methanol (up to 30 g) and the resulting suspension sealed and pressured with 150 psig nitrogen at room temperature, to minimise component vapour losses during reaction. The autoclaves were leak-tested for 45 minutes and all six placed into the pre-heated block together. An initial run had determined that a maximum autoclave pressure (ca. 390 psig at 190° C.) was obtained after 25 minutes in the heated block (30 minutes at 210° C.) and these timings were therefore used as the "T=0" start times for sampling.

Autoclaves were then removed from the block upon reaching their desired sample timings and immediately submerged in ice-water for 15 minutes in order to rapidly quench the reaction. Mass balances were calculated from comparison of the autoclave masses after reaction (vented) with that of the empty autoclave. All samples were analysed for water (coulometric Karl-Fisher) and by GC (Regisil-treated, 50 m DB-1 column, HY 381 method).

Starting molar compositions of succinic acid to methanol of 1:2 and 1:4 were employed at reaction temperatures of 190° C. and 210° C., above the melting point of succinic acid. Data was collected at 10 or 15 minute intervals starting from T=0 giving data for 50 or 75 minutes per run. Mass balances were generally good (>98%) which is likely to be due to good retention of volatiles with the cold-sampling method employed. Methanol levels by GC, however, are still considered unreliable due to the rapid exotherm present upon Regisil treatment of samples. This is likely to be due to the high levels of water present in these samples, typically being in excess of 10 wt %.

The data obtained, which is presented in Tables 1-4 shows trends in the components as expected, with greater conversion to dimethylsuccinate at increased temperature and increased methanol to succinic acid ratio.

TABLE 1

Results of esterification of succinic acid in a 1:4 ratio with methanol at 190° C. in 6 × batch autoclaves

| Run 1 | Experiment Description | 1:4, Methanol:Succinic Acid - 190° C.; 6 × 100 ml Autoclaves | | | | | |
|---|---|---|---|---|---|---|---|
| Autoclave Charge (per Autoclave) | | | | | | | |
| Component | | Mass/g | RMM/g mol−1 | | Mols | | Mol Fraction |
| Methanol | | 15.2 | 32 | | 0.475 | | 80.0% |
| Succinic acod | | 14.0 | 118 | | 0.119 | | 20.0% |
| Totals | | 29.2 | | | 0.593 | | |
| Autoclave Number | N/A | 1 | 2 | 3 | 4 | 5 | 6 |
| Time/min | Initial | 0 | 15 | 30 | 48 | 60 | 75 |
| Mass Discharged/g | | 29.1 | 29.0 | 28.9 | 29.2 | 29.2 | 29.2 |
| Components | | | | | | | |
| Methanol/GC, wt % | 52.033 | 33.304 | 30.328 | 30.221 | 29.618 | 29.014 | 27.828 |
| Dimethyl succinate/GC, wt % | 0.000 | 19.053 | 30.190 | 34.492 | 42.416 | 37.548 | 37.279 |
| Monomethyl succinate/GC, wt % | 0.000 | 28.830 | 22.852 | 21.035 | 19.242 | 18.684 | 18.480 |
| Succinic acid/GC, wt % | 47.967 | 11.093 | 4.591 | 3.153 | 2.533 | 2.332 | 2.281 |

TABLE 1-continued

Results of esterification of succinic acid in a 1:4 ratio with methanol at 190° C. in 6 × batch autoclaves

| | | | | | | |
|---|---|---|---|---|---|---|
| Water/KFT, wt % | 0.000 | 7.172 | 9.792 | 10.344 | 13.245 | 11.682 | 13.407 |
| Sum of Knowns (%) | 100.0 | 99.5 | 97.8 | 99.2 | 107.1 | 99.3 | 99.3 |
| Methanol/mol | 1.626 | 1.041 | 0.948 | 0.944 | 0.926 | 0.907 | 0.870 |
| Dimethylsuccinate/mol | 0.000 | 0.130 | 0.207 | 0.236 | 0.291 | 0.257 | 0.255 |
| Monomethylsuccinate/mol | 0.000 | 0.218 | 0.173 | 0.159 | 0.146 | 0.142 | 0.140 |
| Succinic acid/mol | 0.407 | 0.094 | 0.039 | 0.027 | 0.021 | 0.020 | 0.019 |
| Water/mol | 0.000 | 0.398 | 0.544 | 0.575 | 0.736 | 0.649 | 0.745 |
| MOL Total | 203.3 | 188.2 | 191.1 | 194.1 | 211.9 | 197.4 | 202.9 |
| Methanol/mol fraction | 0.800 | 0.553 | 0.496 | 0.486 | 0.437 | 0.459 | 0.429 |
| Dimethylsuccinate/mol fraction | 0.000 | 0.069 | 0.108 | 0.122 | 0.137 | 0.130 | 0.126 |
| MMS/mol fraction | 0.000 | 0.116 | 0.091 | 0.082 | 0.069 | 0.072 | 0.069 |
| SAC/mol fraction | 0.200 | 0.050 | 0.020 | 0.014 | 0.010 | 0.010 | 0.010 |
| Water/mol fraction | 0.000 | 0.212 | 0.285 | 0.296 | 0.347 | 0.329 | 0.367 |
| Mass Balance (%) | 99.7 | 99.7 | 99.4 | 99.0 | 100.0 | 100.0 | 100.0 |
| Methanol Balance (%) | 100.0 | 101.0 | 100.4 | 101.5 | 97.5 | 98.9 | 93.7 |
| Conversion to Dimethyl succinate ($C_4$ basis) (%) | 0.0 | 29.5 | 49.4 | 55.9 | 63.5 | 61.5 | 61.6 |

TABLE 2

Results of esterification of succinic acid in a 1:2 ratio with methanol at 190° C. in 6 × batch autoclaves

| Run 2 | Experiment Description | 1:2, Methanol:Succinic Acid - 190° C.; 6 × 100 ml Autoclaves | | | | | |
|---|---|---|---|---|---|---|---|
| Autoclave Charge (per Autoclave) | | | | | | | |
| Component | Mass/g | RMM/g mol−1 | Mols | Mol Fraction | | | |
| Methanol | 7.6 | 32 | 0.238 | 66.7% | | | |
| Succinic acid | 14.0 | 118 | 0.119 | 33.3% | | | |
| Totals | 21.6 | g | 0.356 | | | | |
| Autoclave Number | N/A | 1 | 2 | 3 | 4 | 5 | 6 |
| Time/min | Initial | 0 | 15 | 30 | 48 | 60 | 75 |
| Mass Discharged/g | N/A | 21.2 | 21.4 | 21.3 | 21.4 | 21.4 | 21.5 |
| Components | | | | | | | |
| Methanol/GC, wt % | 35.185 | 12.062 | 11.235 | 9.940 | 9.704 | 9.468 | 9.165 |
| Dimethyl succinate/GC, wt % | 0.000 | 27.351 | 32.232 | 35.455 | 35.820 | 36.613 | 36.517 |
| Monomethyl succinate/GC, wt % | 0.000 | 36.783 | 33.649 | 32.319 | 32.464 | 31.168 | 31.767 |
| Succinic acid/GC, wt % | 64.815 | 12.571 | 9.831 | 8.585 | 8.181 | 7.766 | 8.115 |
| Water/KFT, wt % | 0.000 | 10.000 | 12.317 | 13.066 | 13.298 | 13.419 | 13.388 |
| Sum of Knowns (%) | 100.0 | 98.8 | 99.3 | 99.4 | 99.5 | 98.4 | 99.0 |
| Methanol/mol | 1.100 | 0.377 | 0.351 | 0.311 | 0.303 | 0.296 | 0.286 |
| Dimethyl succinate/mol | 0.000 | 0.187 | 0.221 | 0.243 | 0.245 | 0.251 | 0.250 |
| Monomethyl succinate/mol | 0.000 | 0.279 | 0.255 | 0.245 | 0.246 | 0.236 | 0.241 |
| Succinic acid/mol | 0.549 | 0.107 | 0.083 | 0.073 | 0.069 | 0.066 | 0.069 |
| Water/mol | 0.000 | 0.556 | 0.684 | 0.726 | 0.739 | 0.746 | 0.744 |
| MOL Total | 164.9 | 150.5 | 159.4 | 159.7 | 160.3 | 159.4 | 159.0 |
| Methanol/mol fraction | 0.667 | 0.250 | 0.220 | 0.195 | 0.189 | 0.186 | 0.180 |
| Dimethyl succinate/mol fraction | 0.000 | 0.124 | 0.138 | 0.152 | 0.153 | 0.157 | 0.157 |
| Monomethyl succinate/mol fraction | 0.000 | 0.185 | 0.160 | 0.153 | 0.153 | 0.148 | 0.151 |
| Succinic acid/mol fraction | 0.333 | 0.071 | 0.052 | 0.046 | 0.043 | 0.041 | 0.043 |
| Water/mol fraction | 0.000 | 0.369 | 0.429 | 0.455 | 0.461 | 0.468 | 0.468 |
| Mass Balance (%) | N/A | 98.1 | 99.1 | 98.6 | 99.1 | 99.1 | 99.5 |
| Methanol Balance (%) | 100.0 | 102.7 | 98.5 | 97.8 | 97.3 | 97.2 | 96.9 |
| Conversion to DMS ($C_4$ basis) (%) | 0.0 | 32.7 | 39.5 | 43.3 | 43.8 | 45.4 | 44.7 |

TABLE 3

Results of esterification of succinic acid in a 1:4 ratio with methanol at 210° C. in 6 × batch autoclaves

| Run 3 | Experiment Description | 1:4, Methanol:Succinic Acid - 210° C.; 6 × 100 ml Autoclaves | | |
|---|---|---|---|---|
| Autoclave Charge (per Autoclave) | | | | |
| Component | Mass/g | RMM/g mol−1 | Mols | Mol Fraction |
| Methanol | 15.2 | 32 | 0.475 | 80.0% |
| Succinic acid | 14.0 | 118 | 0.119 | 20.0% |
| TOTALS | 29.2 | g | 0.594 | |

TABLE 3-continued

Results of esterification of succinic acid in a 1:4 ratio
with methanol at 210° C. in 6 × batch autoclaves

| Autoclave Number | N/A | 1 | 2 | 3 | 4 | 5 | 6 |
|---|---|---|---|---|---|---|---|
| Time/min | Initial | 0 | 15 | 30 | 48 | 60 | 75 |
| Mass Discharged/g | N/A | 21.2 | 21.4 | 21.3 | 21.4 | 21.4 | 21.5 |
| Components | | | | | | | |
| Methanol/GC, wt % | 52.055 | 26.547 | 28.503 | 27.002 | 27.633 | 28.177 | 27.437 |
| Dimethyl succinate/GC, wt % | 0.000 | 30.617 | 34.013 | 37.628 | 38.581 | 38.136 | 40.186 |
| Monomethyl succinate/GC, wt % | 0.000 | 26.719 | 22.433 | 20.103 | 16.900 | 16.032 | 16.749 |
| Succinic acid/GC, wt % | 47.945 | 5.454 | 3.458 | 2.695 | 1.981 | 1.883 | 1.888 |
| Water/KFT, wt % | 0.000 | 10.222 | 10.809 | 11.561 | 11.785 | 12.221 | 12.657 |
| Sum of Knowns (%) | 100.0 | 99.6 | 99.2 | 99.0 | 96.9 | 96.4 | 98.9 |
| Methanol/mol (%) | 162.7 | 83.0 | 89.1 | 84.4 | 86.4 | 88.1 | 85.7 |
| Dimethyl succinate/mol (%) | 0.0 | 21.0 | 23.3 | 25.8 | 26.4 | 26.1 | 27.5 |
| Monomethyl succinate/mol (%) | 0.0 | 20.2 | 17.0 | 15.2 | 12.8 | 12.1 | 12.7 |
| Succinic acid/mol (%) | 40.6 | 4.6 | 2.9 | 2.3 | 1.7 | 1.6 | 1.6 |
| Water/mol (%) | 0.0 | 56.8 | 60.1 | 64.2 | 65.5 | 67.9 | 70.3 |
| MOL Total | 203.3 | 185.6 | 192.3 | 191.9 | 192.7 | 195.8 | 197.9 |
| Methanol/mol fraction | 0.800 | 0.447 | 0.463 | 0.440 | 0.448 | 0.450 | 0.433 |
| Dimethyl succinate/mol fraction | 0.000 | 0.113 | 0.121 | 0.134 | 0.137 | 0.133 | 0.139 |
| Monomethyl succinate/mol fraction | 0.000 | 0.109 | 0.088 | 0.079 | 0.066 | 0.062 | 0.064 |
| Succinc acid/mol fraction | 0.200 | 0.025 | 0.015 | 0.012 | 0.009 | 0.008 | 0.008 |
| Water/mol fraction | 0.000 | 0.306 | 0.312 | 0.335 | 0.340 | 0.347 | 0.355 |
| Mass Balance (%) | N/A | 72.6 | 73.3 | 72.9 | 73.3 | 73.3 | 73.6 |
| Methanol Balance | 100.0 | 97.7 | 99.2 | 98.4 | 98.6 | 97.3 | 96.9 |
| Conversion to Dimethyl succinate ($C_4$ basis) (%) | 0.0 | 45.8 | 53.9 | 59.5 | 64.6 | 65.5 | 65.8 |

TABLE 4

Results of esterification of succinic acid in a 1:2 ratio with
methanol at 210° C. in 6 × batch autoclaves

| Run 4 | Experiment Description | 1:2, Methanol:Succinic Acid - 210° C.; 6 × 100 ml Autoclaves | | | | | |
|---|---|---|---|---|---|---|---|
| Autoclave Charge (per Autoclave) | | | | | | | |
| Component | Mass/g | RMM/g mol−1 | | Mols | | Mol Fraction | |
| Methanol | 7.6 | 32 | | 0.238 | | 66.7% | |
| Succinic acid | 14.0 | 118 | | 0.119 | | 33.3% | |
| TOTALS | 21.6 | g | | 0.356 | | | |
| Autoclave Number | N/A | 1 | 2 | 3 | 4 | 5 | 6 |
| Time/min | Initial | 0 | 15 | 30 | 48 | 60 | 75 |
| Mass Discharged/g | N/A | 21.3 | 21.4 | 21.4 | 21.3 | 21.6 | 21.4 |
| Components | | | | | | | |
| Methanol/GC, wt % | 35.185 | 11.974 | 10.015 | 9.914 | 10.467 | 9.26 | 9.531 |
| Dimethyl succinate/GC, wt % | 0.000 | 34.477 | 35.544 | 36.478 | 36.246 | 36.944 | 36.116 |
| Monomethyl succinate/GC wt % | 0.000 | 32.082 | 32.488 | 31.692 | 30.645 | 31.474 | 31.242 |
| Succinc acid/GC, wt % | 64.815 | 8.305 | 8.491 | 8.291 | 7.958 | 8.002 | 7.745 |
| Water/KFT, wt % | 0.000 | 11.989 | 12.521 | 12.915 | 13.787 | 13.919 | 14.111 |
| Sum of Knowns (%) | 100.0 | 98.8 | 99.1 | 99.3 | 99.1 | 99.6 | 98.7 |
| Methanol/mol (%) | 110.0 | 37.4 | 31.3 | 31.0 | 32.7 | 28.9 | 29.8 |
| Dimethyl succinate/mol (%) | 0.0 | 23.6 | 24.3 | 25.0 | 24.8 | 25.3 | 24.7 |
| Monomethyl succinate/mol (%) | 0.0 | 24.3 | 24.6 | 24.0 | 23.2 | 23.8 | 23.7 |
| Succinic acid/mol (%) | 54.9 | 7.0 | 7.2 | 7.0 | 6.7 | 6.8 | 6.6 |
| Water/mol | 0.0 | 66.6 | 69.6 | 71.8 | 76.6 | 77.3 | 78.4 |
| MOL Total | 164.9 | 159.0 | 157.0 | 158.8 | 164.1 | 162.2 | 163.1 |
| Methanol/mol fraction | 0.667 | 0.235 | 0.199 | 0.195 | 0.199 | 0.178 | 0.183 |
| Dimethyl succinate/mol fraction | 0.000 | 0.149 | 0.155 | 0.157 | 0.151 | 0.156 | 0.152 |
| Monomethyl succinate/mol fraction | 0.000 | 0.153 | 0.157 | 0.151 | 0.141 | 0.147 | 0.145 |
| Succinic acid/mol fraction | 0.333 | 0.044 | 0.046 | 0.044 | 0.041 | 0.042 | 0.040 |
| Water/mol fraction | 0.000 | 0.419 | 0.443 | 0.452 | 0.467 | 0.477 | 0.481 |
| Mass Balance (%) | N/A | 98.6 | 99.1 | 99.1 | 98.6 | 100.0 | 99.1 |
| Methanol Balance (%) | 100.0 | 102.8 | 99.9 | 99.1 | 96.5 | 95.6 | 94.6 |
| Conversion to Dimethyl succinate ($C_4$ basis) (%) | 0.0 | 43.0 | 43.4 | 44.6 | 45.3 | 45.2 | 45.0 |

The results are illustrated in FIG. 11.

EXAMPLE 2

This example illustrates esterification of mono-methyl succinate with methanol to the di-ester with conversion of almost 90% at a temperature of 190° C.

The monomethyl succinate for this testwork was synthesized in-house from commercially available succinic anhydride and used in its crude form. A 1 dm$^3$ stainless steel autoclave fitted with a bottoms sample point was charged with monomethylsuccinate and made up to 200 psig with nitrogen to minimise component vapour pressures. The reactor was then heated to the desired reaction temperature of 190° C. and methanol pumped to the autoclave via an HPLC pump at a desired rate this was called time zero ("T=0"). Overheads were extracted via an electrically traced heated line to avoid condensation and reflux of the product mixture. This was then condensed and collected via a water cooled catch-pot as is detailed schematically in FIG. 12.

In this arrangement, nitrogen and methanol are fed to a stirred reactor 3 in lines 1 and 2 respectively in which monomethyl succinate is formed. The product stream is removed in line 4 where it is trace heated, the stream is then cooled in condenser 5 such that energy is removed. It is then added to the water cooled catchpot 6

A small gas flow through the system was controlled at a needle/metering valve and bubbler combination 7 after the catch-pot 6 whilst maintaining the reactor pressure at 200 psig. The stream may be cooled against water in condenser 8. Samples from the autoclave itself and of the overheads collected were taken at periodic time intervals and subsequently analysed for water (coulometric Karl-Fisher) and by GC. Autoclave samples were analysed after Regisil treatment on a 50 m DB-1 column, and overheads directly analysed for methanol and dimethyl ether on a 60 m DB-1 column. Masses of all samples and reactor contents were noted to allow mass balances to be calculated.

A reaction temperature of 190° C. and a feed rate of 2 mols methanol per mole of monomethyl succinate per hour was chosen; 3 mols of monomethyl succinate was charged to the autoclave requiring a methanol flow rate of 4.05 mL min$^{-1}$ for the run. A second run was performed at double this flow rate. When the system was at temperature, methanol flow commenced for 120 minute, with periodic sampling throughout the run. The feed composition and conditions used for each test, Runs 1 & 2 are given in Tables 5 & 8 respectively, while the results are given in Tables 6, 7, 9 and 10.

TABLE 5

Feed composition and test conditions for Run 1
at 2 mol Methanol per hour per mol succinic acid

| Experiment ID | Run 1 |
|---|---|
| Experiment Description | 2 mol Methanol hr$^{-1}$ per mol succinic acid charged at 190° C. |

Autoclave Charge (1L Parr)

| Component | Mass, g | RMM/g mol$^{-1}$ | Mol | Mol Fraction |
|---|---|---|---|---|
| Monomethyl succinate (Crude) | 396.0 | 132 | 3.0 | 1.00 |
| Theoretical Yield (of Dimethyl Succinate) | 438.0 | | | |

Crude Monomethyl succinate Analysis

| Component | Mass | RMM/g mol$^{-1}$ | Mols | Mol Fraction |
|---|---|---|---|---|
| Methanol | 0.9 | 32 | 0.027 | 0.01 |
| Dimethyl succinate | 62.5 | 146 | 0.428 | 0.14 |
| Monomethyl succinate | 284.3 | 132 | 2.154 | 0.70 |
| Succinic acid | 47.4 | 118 | 0.402 | 0.13 |
| Water | 0.9 | 18 | 0.048 | 0.02 |
| Total | 396.0 | | 3.060 | |

Methanol Flow

| | | | | |
|---|---|---|---|---|
| Target, molar | 2.0 | mol hr–1 mol$^{-1}$ (Monomethyl succinate) | 6.0 | mol methanol h$^{-1}$ |
| Flow | 192.0 | g hr$^{-1}$ | | |
| Density (methanol) | 0.79 | g ml$^{-1}$ | | |
| Target Flow Rate | 4.05 | ml min$^{-1}$ | | |

TABLE 6

Results of Run 1

| | Experiment ID Run 1 Time, min | | | | | |
|---|---|---|---|---|---|---|
| | 0 | 11 | 22 | 32 | 42 | 52 | 61 |
| Mass Discharged (autoclave), g | 14.5 | 8.3 | 10.4 | 8.2 | 9.8 | 13.6 | 13.0 |
| Methanol Flow Rate/ml min$^{-1}$ | 4.05 | 4.05 | 4.10 | 4.05 | 4.05 | 4.05 | 4.05 |

TABLE 6-continued

Results of Run 1

| | Experiment ID Run 1 Time, min | | | | | | |
|---|---|---|---|---|---|---|---|
| | 0 | 11 | 22 | 32 | 42 | 52 | 61 |
| Reaction Temperature, °C. | 190 | 188 | 188 | 188 | 187 | 188 | 187 |
| System Pressure, psig | 169 | 158 | 165 | 165 | 164 | 163 | 167 |
| Autoclave Components | | | | | | | |
| Methanol/GC, wt % | 1.097 | 3.341 | 6.881 | 11.123 | 12.683 | 12.315 | 11.946 |
| Dimethylsuccinate/GC wt % | 29.214 | 33.185 | 41.273 | 46.738 | 50.692 | 54.770 | 58.932 |
| Monomethylsuccinate/GC wt % | 48.730 | 44.418 | 37.632 | 31.405 | 27.408 | 22.714 | 22.849 |
| Succinic acid/GC, wt % | 18.440 | 15.476 | 9.613 | 5.918 | 4.152 | 2.745 | 2.416 |
| Water/KFT, wt % | 1.950 | 2.789 | 4.081 | 4.386 | 4.518 | 3.773 | 3.205 |
| Sum of Knowns, % | 99.4 | 99.2 | 99.5 | 99.6 | 99.5 | 96.3 | 99.3 |
| Conversion to Dimethyl succinate ($C_4$ Basis), % | 27.6 | 32.7 | 43.5 | 52.6 | 58.8 | 65.8 | 67.6 |
| Overheads Collected, g | 0.0 | 0.0 | 0.1 | 13.4 | 30.8 | 40.8 | 27.4 |
| Overheads analysis | | | | | | | |
| Methanol/GC, wt % | | | | 80.939 | 79.238 | 86.252 | 88.699 |
| Dimethylsuccinate/GC, wt % | | | | 2.613 | 4.100 | | |
| Monomethylsuccinate/GC, wt % | | | | 0.361 | 0.332 | | |
| Succinic acid/GC, wt % | | | | 0.131 | 0.113 | | |
| Water/KFT, wt % | | | | 12.021 | 13.303 | 13.708 | 11.301 |
| Methanol/GC, wt % | | | | | | | |

TABLE 7

Results of Run 1 continued

| | Experiment ID Run 1 (cont'd) Time, min | | | | | | |
|---|---|---|---|---|---|---|---|
| | 72 | 81 | 91 | 101 | 111 | 121 | Final |
| Mass Discharged (autoclave), g | 16.8 | 11.4 | 13.7 | 15.7 | 16.5 | 12.9 | 731.5 |
| Methanol Flow Rate, ml min$^{-1}$ | 4.10 | 4.05 | 4.05 | 4.05 | 4.05 | 4.05 | |
| Reaction Temperature, °C. | 188 | 189 | 188 | 188 | 188 | 190 | |
| System Pressure, psig | 165 | 167 | 166 | 167 | 166 | 161 | |
| Autoclave Components | | | | | | | |
| Methanol/GC, wt % | 11.349 | 13.560 | 12.833 | 12.814 | 12.651 | 13.512 | 13.560 |
| Dimethylsuccinate/GC, wt % | 63.176 | 64.074 | 66.316 | 69.566 | 71.106 | 72.303 | 64.074 |
| Monomethylsuccinate/GC wt % | 20.537 | 18.388 | 17.281 | 15.056 | 13.945 | 12.136 | 18.388 |
| Succinic acid/GC, wt % | 1.879 | 1.506 | 1.275 | 0.957 | 0.759 | 0.535 | 1.506 |
| Water/KFT, wt % | 2.511 | 1.941 | 1.550 | 1.073 | 0.920 | 0.822 | 1.941 |
| Sum of Knowns, % | 99.5 | 99.5 | 99.3 | 99.5 | 99.4 | 99.3 | 99.5 |
| Conversion to Dimethylsuccinate ($C_4$ Basis), % | 71.6 | 74.3 | 76.2 | 79.6 | 81.3 | 83.7 | 88.2 |
| Overheads Collected, g | 40.4 | 30.2 | 35.2 | 35.5 | 37.9 | 36.8 | 292.8 |
| Overheads analysis | | 3.4 | 3.5 | 3.6 | 3.8 | 3.7 | |
| Methanol/GC, wt % | 88.838 | 90.803 | 92.240 | 94.859 | 95.399 | 96.787 | 97.165 |
| Dimethylsuccinate/GC, wt % | | | | | | | |
| Monomethylsuccinate/GC wt % | | | | | | | |
| Succinic acid/GC, wt % | | | | | | | |
| Water/KFT, wt % | 11.162 | 9.197 | 7.760 | 5.141 | 4.601 | 3.213 | 2.835 |
| Methanol/GC, w % | | | | | | | |

TABLE 8

Feed composition and test conditions for Run 2 at 4 mol Methanol per hour per mol succinic acid

| Experiment ID | Run 2 |
| --- | --- |
| Experiment Description | 4 mol Methanol hr$^{-1}$ per mol Succinic acid charged at 190° C. |

Autoclave Charge (1 L Parr)

| Component | Mass/g | RMM/g mol$^{-1}$ | Mols | Mol Fraction |
| --- | --- | --- | --- | --- |
| Monomethylsuccinate (Crude) | 396.0 | 132 | 3.0 | 1.00 |
| Theoretical Yield (of DMS) | 438.0 | | | |

Crude Monomethylsuccinate Analysis

| Component | Mass | RMM/g mol$^{-1}$ | Mols | Mol Fraction |
| --- | --- | --- | --- | --- |
| Methanol | 0.9 | 32 | 0.027 | 0.01 |
| Dimethylsuccinate | 62.5 | 146 | 0.428 | 0.14 |
| Monomethyl succinate | 284.3 | 132 | 2.154 | 0.70 |
| Succinic acid | 47.4 | 118 | 0.402 | 0.13 |
| Water | 0.9 | 18 | 0.048 | 0.02 |
| Total | 396.0 | | 3.060 | |

Methanol Flow

| | | | | |
| --- | --- | --- | --- | --- |
| Target (molar) | 4.0 | mol h$^{-1}$ mol$^{-1}$ (MMS) | 12.0 | mol MeOH h$^{-1}$ |
| Flow | 384.0 | g h$^{-1}$ | | |
| Density (Methanol) | 0.79 | g ml$^{-1}$ | | |
| Target Flow Rate | 8.10 | mL min$^{-1}$ | | |

TABLE 9

Results of Run 2

| | Experiment ID Run 2 Time, min | | | | | |
| --- | --- | --- | --- | --- | --- | --- |
| | 0 | 16 | 25 | 35 | 46 | 59 |
| Mass Discharged (autoclave), g | 14.5 | 9.7 | 5.7 | 10.0 | 5.6 | 7.0 |
| Methanol Flow Rate, ml min$^{-1}$ | 8.10 | 8.10 | 8.10 | 8.10 | 8.10 | 8.10 |
| Reaction Temperature, ° C. | 188 | 184 | 183 | 186 | 187 | 187 |
| System Pressure, psig | | 168 | 170 | 164 | 184 | 163 |
| Autoclave Components | | | | | | |
| Methanol/GC, wt % | 1.097 | 12.053 | 12.823 | 11.526 | 12.693 | 12.709 |
| Dimethylsuccinate/GC, wt % | 29.214 | 42.354 | 44.027 | 49.981 | 53.980 | 59.055 |
| Monomethyl succinate/GC, wt % | 48.730 | 34.006 | 32.199 | 27.850 | 25.688 | 22.081 |
| Succinic acid/GC, wt % | 18.440 | 6.156 | 5.372 | 3.860 | 2.948 | 2.209 |
| Water/KFT, wt % | 1.950 | 3.994 | 4.187 | 3.524 | 2.987 | 2.127 |
| Sum of Knowns, % | 99.4 | 98.6 | 98.6 | 96.7 | 98.3 | 98.2 |
| Conversion to Dimethylsuccinate (C$_4$ Basis), % | 27.6 | 48.4 | 51.0 | 58.4 | 62.7 | 68.5 |
| Overheads Collected, g | 0.0 | 11.1 | 32.1 | 86.4 | 77.4 | 89.5 |
| Overheads, analysis | | | | | | |
| Methanol/GC, wt % | | 77.745 | 86.517 | 89.292 | 91.903 | 92.810 |
| Dimethylsuccinate/GC, wt % | | 5.611 | 5.611 | 6.500 | 8.500 | 10.882 |
| Monomethyl succinate/GC, wt % | | 0.431 | 0.431 | 0.431 | 0.431 | 0.478 |
| Succinic acid/GC, wt % | | | 0.104 | | | 0.114 |
| Water/KFT, wt % | | 22.255 | 13.483 | 10.708 | 8.097 | 7.190 |
| Sum of Knowns | 0.0 | 106.0 | 106.1 | 106.9 | 108.9 | 111.5 |

TABLE 10

Results of Run 2 continued

| Experiment ID | Run 2 (cont'd) | | | | |
| --- | --- | --- | --- | --- | --- |
| Time, min | 73 | 90 | 105 | Final | |
| Mass discharged (autoclave), g | 11.3 | 9.0 | 6.0 | 316.3 | |
| Methanol Flow Rate, ml min$^{-1}$ | 8.10 | 8.10 | 8.10 | | |
| Reaction Temperature, ° C. | 187 | 187 | 187 | | |

TABLE 10-continued

Results of Run 2 continued

| System Pressure, psig | 160 | 154 | 162 | |
|---|---|---|---|---|
| Autoclave Components | | | | |
| Methanol/GC, wt % | 13.647 | 12.668 | 14.231 | 13.412 |
| Dimethylsuccinate/GC, wt % | 64.972 | 68.887 | 70.613 | 75.011 |
| Monomethyl succinate/GC, wt % | 17.891 | 14.889 | 12.290 | 9.788 |
| Succinic acid/GC, wt % | 1.234 | 0.836 | 0.577 | 0.322 |
| Water/KFT, wt % | 1.265 | 0.795 | 0.537 | 0.529 |
| Sum of Knowns, % | 99.0 | 98.1 | 98.2 | 99.1 |
| Conversion to Dimethylsuccinate ($C_4$ Basis), % | 75.3 | 79.7 | 83.2 | 87.0 |
| Overheads Collected, g | 103.9 | 126.8 | 103.8 | 19.6 |
| Overheads, analysis | | | | |
| Methanol/GC, wt % | 95.608 | 97.724 | 98.185 | 90.656 |
| Dimethylsuccinate/GC, wt % | 11.500 | 12.399 | 13.399 | 16.000 |
| Monomethyl succinate/GC, wt % | 0.478 | 0.471 | 0.471 | 0.471 |
| Succinic acid/GC, wt % | | 0.142 | | |
| Water/KFT, wt % | 4.392 | 2.276 | 1.815 | 9.344 |
| Sum of Knowns | 112.0 | 113.0 | 113.9 | 116.5 |

EXAMPLE 3

This example demonstrates semi-continuous conversion of mono-methyl succinate and succinic acid to di-methyl succinate with a low acid product taken overhead.

To prepare feed for the test an autoclave was charged with 3000 g bio-succinic acid and 2440 g methanol and heated to 120° C. under an inert atmosphere. Once at temperature the vessel was pressurised to 8-9 bar(g) and the contents held for 30 minutes prior to discharge. This was to prevent over conversion to dimethyl succinate. The resulting composition was found to be: (wt %)

Methanol—29.2%
Monomethyl succinate—44.88%
Water—1.87%
Dimethyl succinate—17.83%
Succinic acid—5.43%

The distillation was performed using a 1" diameter glass column containing nine pieces of Sulzer type EX structured packing, operated in continuous mode. A Liebig condenser was used on the top of the column to cool/condense the overheads. Heating tape was also applied to the column walls allowing then to be held at temperature to assist in entraining the Dimethyl succinate overhead and prevent it being boxed up in the reactor and/or in the column.

The reboiler was an insulated 2 liter round-bottomed flask, heated using an isomantle, which would also provide the reaction volume. The temperature of the isomantle was controlled using a Watlow burst fire module with a k type thermocouple attached to the skin of the vessel. A further k type thermocouple was located inside the reboiler to determine the actual process temperature.

The column temperature was controlled at 210° C. The flask was charged with 870 g of the above feed and heated to 230° C. Once at temperature the feed was introduced via a constametric pump and sampled every hour attempting to maintain 100% mass balance by varying the feed rate (rate maintained between 0.8-1.2 mLs/min).

Analysis of the chemical composition of the flask was carried out by gas chromatography (GC) using N,O-Bis trimethylsilylacetamide (Regisil) to allow the resolution of acidic species to be achieved. The level of methanol, dimethyl succinate, monomethyl succinate, and succinic acid were determined (Sil8 column 50 m×0.32 mm). Flask samples were also analysed for acid content by means of a base titration with 0.1N KOH using methanolic phenolphthalein indicator solution. Water analysis was performed on HP08 which as was fitted with a thermal conductivity detector (TCD).

Overheads were analysed for water (HP08) and dimethyl succinate/methanol AS08 (30 m×0.32 mm DB-FFAP column). Overhead samples were also analysed for acid content by means of a base titration with 0.1N KOH using methanolic phenolphthalein indicator solution.

The separation of dimethyl succinate from the heavier boiling acid species of monomethyl succinate and succinic acid was successful. Acid levels throughout remained low (<0.2 wt % as monomethyl succinate) in the overheads with a dimethyl succinate concentration of >60 wt % observed as shown in Tables 11 and 12.

TABLE 11

Example 3 Results

| | | Hours on line | | | | | | | | |
|---|---|---|---|---|---|---|---|---|---|---|
| | | 0.00 | 0.75 | 1.00 | 1.25 | 1.50 | 1.75 | 2.00 | 2.75 | 3.75 | 6.25 |
| Temperatures | | | | | | | | | | | |
| Skin | ° C. | 280 | 280.3 | 280.2 | 279.8 | 281.3 | 280.7 | 280.2 | 280.3 | 280 | 279.8 |
| Pot | ° C. | 232.2 | 231.1 | 230.6 | 231.7 | 232.4 | 233.7 | 231.9 | 228.2 | 231.2 | 237.6 |
| Column Heater | ° C. | 215 | 214.2 | 212.8 | 212.7 | 212.6 | 212.3 | 212.6 | 212.4 | 212.8 | 209.9 |
| Overheads | ° C. | 115 | 170 | 173 | 153 | 151 | 167 | 163 | 170 | 170 | 144 |
| Rates | | | | | | | | | | | |
| Feed - set | ml/min | 0.50 | 0.50 | 0.70 | 0.70 | 0.70 | 0.70 | 0.70 | 0.70 | 0.70 | 0.7 |
| Feed - actual | ml/min | 0.50 | 0.52 | 0.75 | 0.74 | 0.74 | 0.74 | 0.74 | 0.75 | 0.75 | 0.689 |
| Overhead sample weight | g | | 18.55 | 23.18 | 8.41 | 4.91 | 18.04 | 14.57 | 34.78 | 43.66 | 25.464 |
| Overheads Analysis | | | | | | | | | | | |
| Methanol | wt % | | 11.89 | | 68.22 | 26.10 | 26.10 | 21.38 | 27.48 | 33.54 | 35.12 |
| Dimethyl succinate | wt % | | 78.77 | | 28.24 | 69.02 | 69.02 | 75.23 | 68.39 | 61.12 | 55.68 |

TABLE 11-continued

Example 3 Results

| | | Hours on line | | | | | | | | |
|---|---|---|---|---|---|---|---|---|---|---|
| | | 0.00 | 0.75 | 1.00 | 1.25 | 1.50 | 1.75 | 2.00 | 2.75 | 3.75 | 6.25 |
| Water | wt % | | 8.83 | 8.83 | 3.54 | 4.87 | 4.87 | 3.39 | 4.15 | 5.34 | 7.12 |
| Acid | wt % | | 0.17 | 0.17 | 0.16 | 0.12 | 0.12 | 0.12 | 0.19 | 0.13 | 0.12 |
| Pot Analysis | | | | | | | | | | | |
| Methanol | wt % | | 0.00 | | | | | 0.10 | | 0.00 | |
| Dimethyl succinate | wt % | | 37.72 | | | | | 28.24 | | 31.29 | |
| Monomethyl succinate | wt % | | 41.83 | | | | | 45.27 | | 51.75 | |
| Succinic acid | wt % | | 4.62 | | | | | 5.90 | | 7.38 | |
| Water | wt % | | 0.00 | | | | | 0.00 | | 0.00 | |
| Others | wt % | | 15.83 | | | | | 20.48 | | 9.58 | |

TABLE 12

Example 3 Results Continued

| | | Hours on line | | | | | | | | |
|---|---|---|---|---|---|---|---|---|---|---|
| | | 7.10 | 7.35 | 7.76 | 8.76 | 9.40 | 9.93 | 10.85 | 11.43 | 11.85 |
| Temperatures | | | | | | | | | | |
| Skin | ° C. | 279.9 | 279.8 | 280.5 | 279.6 | 263.8 | 274.5 | 280 | 279.6 | 280 |
| Pot | ° C. | 232.5 | 233.6 | 234.1 | 239.2 | 230.4 | 243.1 | 235.8 | 236 | 236 |
| Column Heater | ° C. | 212.2 | 212.4 | 212.2 | 233.9 | 233 | 216 | 206.6 | 205.1 | 214.4 |
| Overheads | ° C. | 65 | 90 | 175 | 162 | 142 | 66 | 154 | 177 | 160 |
| Rates | | | | | | | | | | |
| Feed - set | ml/min | 0.7 | 0.7 | 0.7 | 0.7 | 1 | 1 | 0.7 | 0.7 | 0.7 |
| Feed - actual | ml/min | 0.7637 | 0.7637 | 0.7659 | 0.75 | 1.264 | 1.264 | 0.793 | 0.793 | 0.7 |
| Overhead sample weight | g | 9.8116 | 10.636 | 41.28 | 103.5 | 36.675 | 17.9995 | 17.3475 | 42.03 | 12.33 |
| Overheads Analysis | | | | | | | | | | |
| Methanol | wt % | 84.9 | 90.14 | 22.75 | 10.97 | 19.77 | 41.07 | 31.93 | 20.97 | 21.98 |
| Dimethyl Succinate | wt % | 10.01 | 1.01 | 64.08 | 84.53 | 74.13 | 49.08 | 49.55 | 72.31 | 71.14 |
| Water | wt % | 5.02 | 8.72 | 13.18 | 3.91 | 6.10 | 9.85 | 18.51 | 6.71 | 6.88 |
| Acid | wt % | 0.36 | 0.24 | 0.14 | 0.16 | 0.15 | 0.24 | 0.24 | 0.15 | 0.15 |
| Pol Analysis | | | | | | | | | | |
| Methanol | wt % | 0.00 | | 0.16 | 0.12 | | 0.00 | | 0.00 | |
| Dimethyl Succinate | wt % | 31.08 | | 28.81 | 2.56 | | 24.41 | | 18.23 | |
| Monomethyl succinate | wt % | 48.91 | | 50.40 | 53.98 | | 48.11 | | 54.88 | |
| Succinic acid | wt % | 8.23 | | 7.09 | 8.61 | | 12.54 | | 17.52 | |
| Water | wt % | 0.00 | | 0.00 | 0.00 | | 0.00 | | 0.00 | |
| Others | wt % | 11.77 | | 13.56 | | | 14.94 | | 9.37 | |

EXAMPLE 4

This example demonstrates an extended test replicating the results of Example 3 to achieve near steady state conditions.

The feed was prepared as detailed in Example 3. The resulting composition was found to be: (wt %)

Methanol—15.42%
Monomethyl succinate—24.69%
Water—14.02%
Dimethyl succinate—40.78%
Succinic acid—3.54%

A 1 liter round-bottomed flask (RBF) was charged with 820.9 g of the above feed. The reaction was performed as in Example 3, except that the 1" wide distillation column now contained twelve pieces of Sulzer packing to aid separation and the column had two heated zones enabling the temperature of both the top and bottom areas of the column to be controlled. The reaction was sampled periodically as described in Example 3.

Dimethyl succinate levels in the overheads were relatively steady throughout the test and acid (as monomethyl succinate) in the overheads was low (<0.1 wt %). An increase in the column heater temperature at the end of the test, leading to flooding of the column demonstrates how overheating and reduced separation efficiency will lead to increased acid carryover into the overheads. FIGS. 14, 15 and 16 show the overheads composition, flash composition and key temperatures over the duration of the test.

EXAMPLE 5

This example demonstrates further distillation of the overheads from Example 4 to separate dimethyl succinate from methanol and water.

The overheads collected during Example 4 were bulked together and 1471.4 g were charged to a 2 L round bottom flask and distilled batch wise using the column set-up described in Example 3. Overhead samples and pot samples were taken every hour and the samples were analysed on GC AS08 for methanol and dimethyl succinate concentration and water analysis (Karl Fischer volumetric titration). Some samples were also analysed for acid content by means of a base titration with 0.1N KOH using methanolic phenolphthalein indicator solution.

FIGS. 17, 18 and 19 show the overheads composition, pot composition and temperatures respectively over the course of the test. Note in FIG. 17 how water is not completely separable from dimethyl succinate by simple distillation, due to the existence of a low boiling azeotrope.

The invention claimed is:

1. A process for the production of dialkyl succinate from a bio-succinic acid feedstock comprising the steps of:
   (a) feeding bio-succinic acid to a point at or near the bottom of a reaction distillation zone column operated at temperatures and pressures to enable esterification of the succinic acid and passing said stream co-currently with upflowing alkanol such that said esterification reaction occurs;
   (b) removing an overhead vapour stream from at or near the top of the reaction distillation zone column comprising di-ester, alkanol, water of esterification and organic components and passing said stream to an alkanol separation column where the alkanol is separated from the water of esterification and from the organic components;
   (c) removing a side draw from the alkanol separation column from a point below the feed point thereto, said side draw comprising partially immiscible organic and aqueous phases;
   (d) passing said side draw to phase separation apparatus where the partially immiscible organic and aqueous phases are separated;
   (e) passing said organic phase to a column where the dialkyl succinate is separated from residual water and other organic components; and
   (f) recovering the dialkyl succinate.

2. A process according to claim 1 wherein the bio-succinic acid is added to a pre-reactor prior to being supplied to the reaction distillation zone column.

3. A process according to claim 2 wherein the pre-reactor is a continuous stirred tank reactor.

4. A process according to claim 2 wherein a product from the pre-reactor is passed to a plug flow reaction vessel before being fed to the reaction distillation zone column.

5. A process according to claim 1 wherein the reaction distillation zone column is operated at an overheads pressure of about 1.3 bara to about 10 bara.

6. A process according to claim 1 wherein reaction distillation zone column operates at a temperature of about 80° C. to about 300° C.

7. A process according to claim 1 wherein the reaction in the reaction distillation zone column is carried out in the absence of a catalyst such that it is auto-catalysed.

8. A process according to claim 1 wherein the reaction in the reaction distillation zone column is carried out in the presence of a catalyst.

9. A process according to claim 8 wherein the catalyst is located in the upper stages of the reaction distillation zone column.

10. A process according to claim 1 wherein the stream removed from at or near the top of the reaction distillation zone column is passed through a condenser before being passed to the alkanol separation column.

11. A process according to claim 1 wherein the stream removed from the reaction distillation zone column is supplied to a central region of the alkanol separation column.

12. A process according to claim 1 wherein the alkanol separated in the alkanol separation column is recycled to the reaction distillation zone column and/or to the pre-reactor where present.

13. A process according to claim 1 wherein the desired di-ester is removed from the alkanol separation column as a side draw.

14. A process according to claim 13 wherein the side draw is removed from the alkanol separation column at a point below the feed point.

15. A process according to claim 1 wherein the phase separation apparatus is a decanter.

16. A process according to claim 1 wherein the aqueous phase from the phase separation apparatus is returned to the alkanol separation column.

17. A process according to claim 16 wherein the returned aqueous phase is returned to a point below the side draw point.

18. A process according to claim 1 wherein the organic phase from the phase separation apparatus is passed to the reaction distillation column.

19. A process according to claim 18 wherein the dialkyl succinate is removed from the reaction distillation column as a side draw.

20. A process according to claim 1 wherein the organic phase from the phase separation apparatus is passed to a dialkyl succinate separation column.

21. A process according to claim 20 wherein the dialkyl succinate separation column is operated at mild vacuum.

22. A process according to claim 20 wherein the dialkyl succinate is removed from the dialkyl succinate separation column as a bottom stream.

23. A process according to claim 20 wherein any water separated in the dialkyl succinate separation column is recycled to the alkanol separation column.

24. A process according to claim 20 wherein any butanol is removed as a liquid draw from the dialkyl succinate separation column.

25. A process according to claim 20 wherein an overhead from the dialkyl succinate separation column and passed to a second phase separation apparatus.

26. A process according to claim 25 wherein the second phase separation apparatus is a decanter.

27. A process according to claim 25 wherein the aqueous phase from the second phase separation apparatus is returned to the alkanol separation column.

28. A process according to claim 22 wherein the organic phase from the second phase separation apparatus is passed to a dialkyl succinate/butanol separation column.

29. A process according to claim 1 wherein a portion of the diester produced in the reaction distillation column zone is removed as a liquid side draw.

* * * * *